(12) United States Patent
Han et al.

(10) Patent No.: US 8,105,471 B1
(45) Date of Patent: Jan. 31, 2012

(54) NANOFLUIDICS FOR BIOSEPARATION AND ANALYSIS

(76) Inventors: Sang M. Han, Albuquerque, NM (US); Steven R. J. Brueck, Albuquerque, NM (US); Cornelius F. Ivory, Pullman, WA (US); Gabriel P. Lopez, Albuquerque, NM (US); Dimiter N. Petsev, Albuquerque, NM (US)

( * ) Notice: Subject to any disclaimer, the term of this patent is extended or adjusted under 35 U.S.C. 154(b) by 1347 days.

(21) Appl. No.: 11/184,540

(22) Filed: Jul. 19, 2005

Related U.S. Application Data

(60) Provisional application No. 60/589,200, filed on Jul. 19, 2004.

(51) Int. Cl.
*G01N 27/447* (2006.01)
*G01N 27/453* (2006.01)
(52) U.S. Cl. ......... 204/451; 204/601; 204/459; 204/548
(58) Field of Classification Search .......... 204/450–455, 204/600–605, 459, 548
See application file for complete search history.

(56) References Cited

U.S. PATENT DOCUMENTS

| | | | |
|---|---|---|---|
| 3,855,133 A | 12/1974 | Roehsler | |
| 4,801,380 A | 1/1989 | Parker et al. | |
| 4,814,082 A | 3/1989 | Wrasidlo | |
| 4,814,088 A | 3/1989 | Kutowy et al. | |
| 4,902,424 A | 2/1990 | Wrasidlo | |
| 4,935,141 A | 6/1990 | Buck et al. | |
| 4,969,998 A | 11/1990 | Henn | |
| 5,013,337 A | 5/1991 | Bedard et al. | |
| 5,019,263 A | 5/1991 | Haag et al. | |
| 5,092,972 A * | 3/1992 | Ghowsi | 204/454 |
| 5,130,025 A | 7/1992 | Lefebvre et al. | |
| 5,145,584 A | 9/1992 | Swamikannu | |
| 5,266,207 A | 11/1993 | Boye et al. | |
| 5,302,264 A | 4/1994 | Welch et al. | |
| 5,474,675 A | 12/1995 | Kupka | |
| 5,580,435 A * | 12/1996 | Kovacs | 204/603 |
| 5,716,527 A | 2/1998 | Deckman et al. | |
| 5,723,031 A | 3/1998 | Durr et al. | |
| 5,753,014 A | 5/1998 | Van Rijn | |
| 5,786,830 A | 7/1998 | Su et al. | |
| 5,798,042 A | 8/1998 | Chu et al. | |
| 5,938,923 A | 8/1999 | Tu et al. | |
| 5,993,661 A | 11/1999 | Ruckenstein et al. | |
| 6,043,177 A | 3/2000 | Falconer et al. | |
| 6,044,981 A | 4/2000 | Chu et al. | |

(Continued)

OTHER PUBLICATIONS

CAPLUS abstract of Ramsey et al. "Molecular transport through nanometer confined channels," Micro Total Analysis Systems 2002, Proceedings of the mTAS 2002 Symposium, 6th, Nara, Japan, Nov. 3-7, 2002, vol. 1, 314-316.*

(Continued)

*Primary Examiner* — Alex Noguerola
(74) *Attorney, Agent, or Firm* — Gonzales Patent Services; Ellen M. Gonzales

(57) ABSTRACT

The invention includes nanochannel devices and methods for using such nanochannel devices for separating molecules, ions and biomolecules. The nanochannel devices have at least one nanochannel through which fluid can move, wherein ionic double layers form in the fluid near walls of the nanochannel and those ionic double layers overlap within the nanochannel. Electrical voltage can be applied to the nanochannel to modify an electrostatic potential in the nanochannel and thereby control movement of ions and biomolecules through the nanochannel. The invention also includes arrays and networks of such nanochannel devices.

69 Claims, 15 Drawing Sheets

U.S. PATENT DOCUMENTS

| | | | |
|---|---|---|---|
| 6,051,517 | A | 4/2000 | Funke et al. |
| 6,060,415 | A | 5/2000 | Chao et al. |
| 6,090,289 | A | 7/2000 | Verduijn et al. |
| 6,100,393 | A | 8/2000 | Lopez Ortiz et al. |
| 6,113,794 | A | 9/2000 | Kumar et al. |
| 6,113,795 | A | 9/2000 | Subramaniam et al. |
| 6,177,373 | B1 | 1/2001 | Sterte et al. |
| 6,190,638 | B1 | 2/2001 | Anthonis et al. |
| 6,243,348 | B1 | 6/2001 | Goodberlet |
| 6,264,044 | B1 | 7/2001 | Meyering et al. |
| 6,296,752 | B1 | 10/2001 | McBride et al. |
| 6,361,671 | B1 | 3/2002 | Mathies et al. |
| 6,368,871 | B1 | 4/2002 | Christel et al. |
| 6,660,147 | B1 * | 12/2003 | Woudenberg et al. ........ 204/455 |
| 7,220,345 | B2 | 5/2007 | Bohn et al. |
| 7,465,381 | B2 | 12/2008 | Lopez et al. |
| 2003/0127329 | A1 * | 7/2003 | DeVoe et al. ................. 204/454 |
| 2004/0262159 | A1 | 12/2004 | Martin et al. |
| 2006/0169587 | A1 | 8/2006 | Lopez et al. |
| 2006/0191831 | A1 * | 8/2006 | Hansford et al. ............. 210/143 |

OTHER PUBLICATIONS

Choi et al., "Electrokinetic flow-induced currents in silica nanofluidic channels," Journal of Colloid and Interface Science 333 (2009) 672-678.*

Vinther et al. "Radial pH distribution during capillary electrophoresis with electroosmotic flow—Analysis with high ionic strength buffers," Journal of Chromatrography, 589 (1992) 315-319.*

"U.S. Appl. No. 10/958,113, Non-Final Office Action mailed Aug. 9, 2007", 15 pgs.

"U.S. Appl. No. 10/958,113, Notice of Allowance mailed Feb. 14, 2008", 9 pgs.

"U.S. Appl. No. 10/958,113, Notice of Allowance mailed Aug. 4, 2008", 9 pgs.

"U.S. Appl. No. 10/958,113, Amendment and Response filed Dec. 7, 2007 to non-final Office Action mailed Aug. 9, 2007", 19 pages.

Klett, O., et al., "Elimination of High-Voltage Field Effects in End Column Electrochemical Detection in Capillary Electrophoresis by Use of on-chip Micro band Electrodes", *Analytical Chemistry*; 73(8), Dep. of Analytical Chem., Uppsala University, PO Box 531, SE-751 21, Sweden, (Apr. 15, 2001), 1909-1915.

Vandaveer IV, W. R., et al., "Recent Developers in Amperometric Detection for Microchip Capillary Electrophoresis", *Electrophoresis*: 23, Dep. of Pharmaceutical Chem., Univ. of Kansas, KS, (2002), 3667-3677.

Wang, J., et al., "Integrated Electrophoresis Chips/ Amperometric Detection with Sputtered Gold Working", *Anal. Chem.*; 71(17), Dep. of Chem and BoiChem., New Mexico State University, Las Cruces, NM, (Sep. 1, 1999), 3901-3904.

* cited by examiner

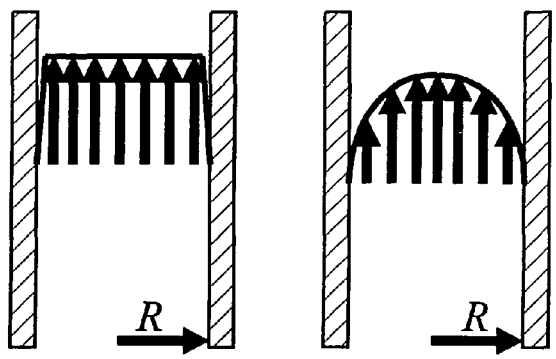
*Fig.5A*   *Fig.5B*
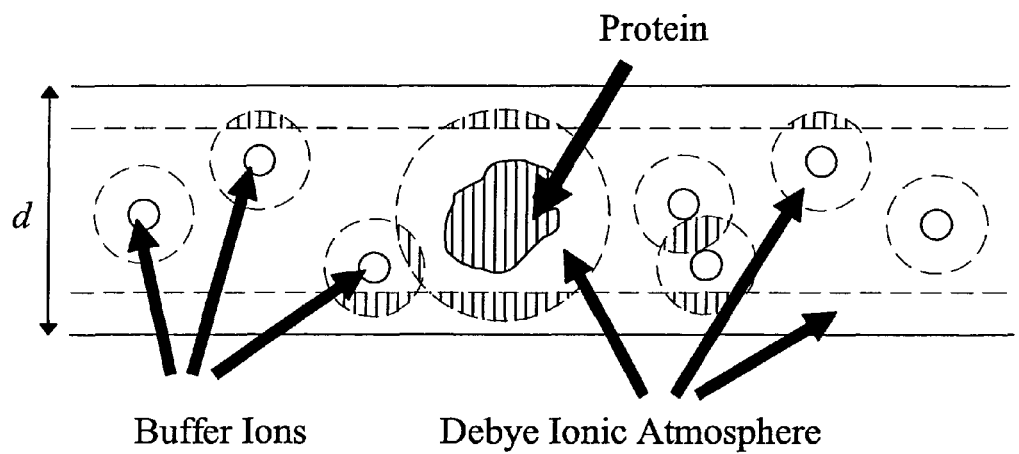
*Fig.6*

FIG. 10
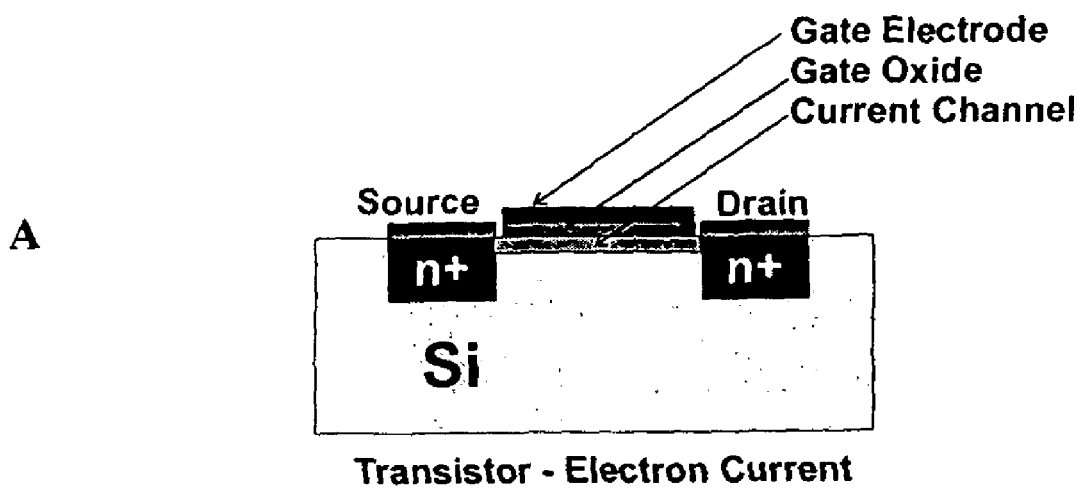
A
Transistor - Electron Current
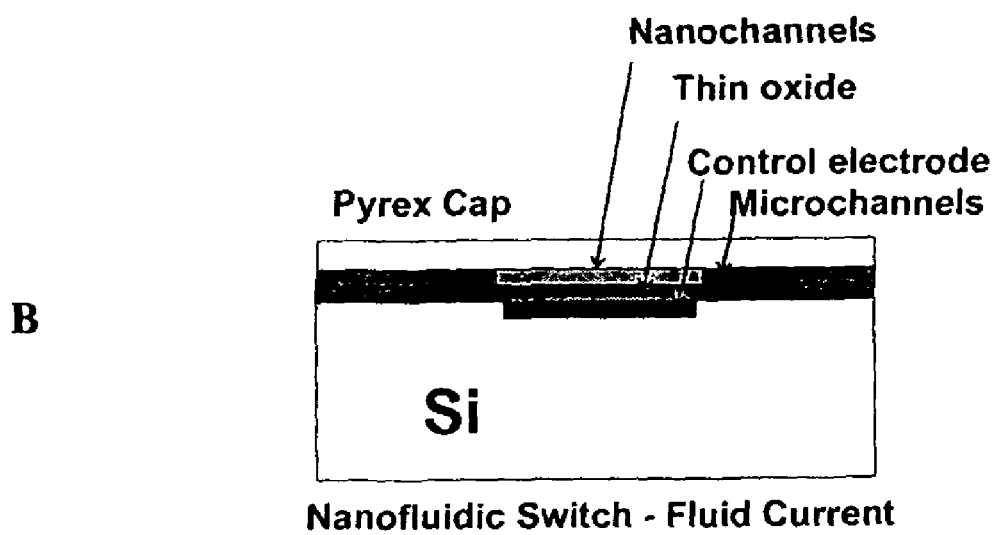
B
Nanofluidic Switch - Fluid Current

NANOFLUIDICS FOR BIOSEPARATION AND ANALYSIS

This application claims benefit of the filing date of U.S. Provisional Application Ser. No. 60/589,200, filed Jul. 19, 2004, the contents of which are incorporated herein in their entirety.

GOVERNMENT FUNDING

The invention described herein was developed with support from the National Science Foundation Grant Nos. CTS-0304237; CTS-0404124; and DGE-00114319. The U.S. Government has certain rights in the invention.

FIELD OF THE INVENTION

The invention relates to chip-based nanofluidics systems useful for separating and analyzing molecules, including complex biological molecules.

BACKGROUND OF THE INVENTION

Polyacrylamide gel electrophoresis (PAGE) remains the standard for protein separation and identification. Nevertheless, the separation strategies that rely on this technique are hampered by (1) inconvenience and irreproducibility in preparation of the variety of gels needed for the separations, (2) limited resolution and dynamic range of biomolecular separations, (3) susceptibility of the polymer to degradation under high electric fields, (4) limitations in their compatibility with mass spectrometric identification of proteins, and (5) relatively large volumes and concentrations of material needed for detection of separated species. Gradient PAGE techniques are recognized to have good resolution and dynamic range, but their utility is greatly hampered by the need for cumbersome gel synthesis protocols and lack of reproducibility.

Thus new devices and methods for separating and analyzing biomolecules are needed.

SUMMARY OF THE INVENTION

Nanostructured separation matrices are formed and may be used to separate molecules. The devices of the invention can be used to separate molecules including native and detergent-solubilized protein mixtures, protein complexes, nucleic acids (DNA and/or RNA), crystal clusters, nanoparticles, subcellular organelles, viruses, phage, and the like. The devices can be used in a variety of separation strategies, including isoelectric focusing, isotachophoresis, affinity techniques, gradient techniques, and multidimensional separation strategies based on multidimensional combinations of these techniques. Significantly, the devices of the invention can be manufactured into networks of nanochannel devices that are integrated with detection systems, thereby permitting evaluation of the purity of biomolecules at various stages of the purification or analytical procedure and further separation of the biomolecules if desired.

Thus, one aspect of the invention is a device comprising at least one nanochannel through which a fluid can move, wherein an ionic double layer forms in the fluid near each wall of the nanochannel and an ionic double layer formed along one wall of the nanochannel substantially overlaps an ionic double layer formed along an opposing wall of the nanochannel; and wherein a first electrical potential difference can be applied to the fluid at the ends of the nanochannel to induce electrokinetic transport along the nanochannel.

In some embodiments, a second electrical potential difference can be applied between at least a segment of a nanochannel wall and the fluid at one end of the nanochannel to modify the electrostatic potential distribution within the nanochannel and thereby modify the movement of ions and molecules through the nanochannel. Moreover, in other embodiments, at least one portion of one wall of the nanochannel is multilayered with an electrically conducting layer, which can be connected to the second electrical potential. The electrically conducting layer can be a semi-conductor. Alternatively, electrically conducting layer can be metal. In some embodiments, the electrically conducting layer is silicon on insulator. In further embodiments, an insulating or selectively conducting layer is interposed between the electrically conducting layer and the fluid within the nanochannel. Such a selectively conducting layer has at least a 10-fold difference in conductivity relative to the electrically conducting layer. In some embodiments, a selectively conducting layer has at least a 100-fold, or a 1000-fold, or a 10,000, or even a 100,000 difference in conductivity relative to the electrically conducting layer. In further embodiments, a selectively conducting layer has at least a $10^6$ difference in conductivity relative to the electrically conducting layer.

Another aspect of the invention is a nanochannel device with multiple, electrically-isolated, portions of the nanochannel wall connected to multiple electrical potential difference sources referenced to the potential in the fluid at one end of the nanochannel to modify the electrostatic potential distribution within the nanochannel and thereby modify the movement of ions and biomolecules through the nanochannel. Thus, the nanochannel wall surface charge density can electrically adjusted by changing the second electrical potential difference.

In some embodiments, the nanochannel wall surface charge density can be separately or additionally chemically adjusted. For example, the nanochannel wall surface charge density can be chemically adjusted by interaction with a protonating or deprotonating agent, or by interaction with acid or base. In other embodiments, the nanochannel wall surface charge density is chemically adjusted by interaction with hydroxyl ions, amines, ammonium ions, formic acid, barium ions, polylysine, or polyelectrolytes.

Moreover, the fluid near nanochannel walls can have a different pH than the fluid in the nanochannel's center. Such a pH difference between the fluid at the walls and the fluid in the center of the nanochannels is described herein as the transverse pH difference. The average transverse pH difference between the walls and the center of the nanochannel can, for example, be about 0.01 to about 2.0 pH units. The pH near the nanochannel walls can be higher or lower than the pH near the center of the nanochannel. In some embodiments, the average transverse pH difference between the walls and the center of the nanochannel varies along the nanochannel's length. For example, the average transverse fluid pH can change as the nanochannel's width changes along the nanochannel's length. Moreover, the average transverse fluid pH can change when the second electrical potential difference is applied to a portion of wall of nanochannel. Thus, the average transverse fluid pH can change along the length of a nanochannel and from one nanochannel to another (second) nanochannel.

Another aspect of the invention is a device comprising at least one nanochannel through which a fluid can move, wherein an ionic double layer forms in the fluid near each wall of the nanochannel and an ionic double layer formed along one wall of the nanochannel substantially overlaps an ionic double layer formed along an opposing wall of the nanochannel; and wherein a hydrostatic pressure can be applied to the fluid at one end of the nanochannel to induce transport of molecules and ions along the nanochannel. A second electrical potential difference can also be applied between at least a segment of a nanochannel wall and the fluid at one end of the nanochannel to modify the electrostatic potential distribution within the nanochannel and thereby modify the movement of ions and molecules through the nanochannel.

Another aspect of the invention is a network that includes multiple devices of the invention. Such a network can include electronic components that control the first and/or second electrical potential differences applied to each device, and multiple detectors for observing ionic or molecular transport within each device. Thus the network including multiple devices, can also include electronic components that can control the first and second electrical potential differences applied to each of the devices, and multiple detectors for observing ionic or molecular transport within each device, wherein the electronic components are interconnected with the detectors to adjust the first and second potential differences in response to the observed ionic or molecular transport within each device.

Another aspect of the invention is a method for separating molecules that involves flowing a sample comprising the molecules through at least one nanochannel of at least one nanochannel device, applying a first potential difference between fluid at two ends of the at least one nanochannel, and observing separation of the molecules after portions of the sample have moved at least part way through the at least one nanochannel; wherein an ionic double layer that forms along one wall of the nanochannel substantially overlaps an ionic double layer that forms along an opposing wall of the nanochannel. A second potential difference can be applied between at least one portion of one wall of each nanochannel and the fluid at one end of the nanochannel to modify an electrostatic potential distribution within the nanochannel and thereby modify the movement of molecules through the nanochannel. Applying the second electrical potential difference can include pulsing an electrical voltage. Moreoever, the second electrical potential difference can vary along the length of at least one nanochannel. In some embodiments, the sample flows through an interconnected network of nanochannel devices. The methods of the invention can be adapted to include isoelectric focusing, isotachophoresis, zone electrophoresis, gradient-channel electrophoresis, FET isotachophoresis, FET-affinity chromatography, FET-electrochromatography, size exclusion chromatography, or ion-exchange chromatography. Ionic/molecular separation can observed by confocal microscopy or by observing a detectable label on a molecule of interest or by measuring current along a section of the nanochannel. In other embodiments, ionic/molecular separation can be observed by infrared spectroscopy, fluorimetry, light microscopy, ultraviolet microscopy, refractometry, Fourier transform infrared (FTIR) spectroscopy, nanomachined-waveguide-assisted Fourier transform infrared spectroscopy (NWA-FTIRS), or electrochemical impedance spectroscopy (EIS).

DESCRIPTION OF THE FIGURES

FIG. 2A shows narrow channels that are about 700 nm deep. FIG. 2B shows the silicon walls (dark) overlaid on the originally oxidized (light gray) array of channels. Upon etching the silicon oxide with hydrogen fluoride, the silicon walls remain.

FIG. 3A and FIG. 3B are SEM micrographs of the photoresist pattern on opposite ends of a chip. Thus, width gradients can be generated in nanochannels on a single device or chip.

FIG. 5A-B illustrate electro-osmotic velocity profiles for thin, $kR >> \geq 1$, (FIG. 5A), and overlapping, $kR \geq 1$, electrical double layers. The "double layer" refers to the dual electrical potentials deriving from the two charged walls of the channels that interact with the ions in the fluid phase. FIG. 5A shows that the electro-osmotic velocity is generally uniform across the width of the channels when little difference in charge exists between the channel walls and the fluid phase. FIG. 5B shows that the electro-osmotic velocity is far from uniform across the width of the channels when a large difference in charge exists between the channel walls and the fluid phase.

FIG. 6 illustrates the flow of protein solution in confined geometry (i.e. microfluidic or nanofluidic channel) with diameter (d). The overlap of the ionic atmospheres indicates strong interactions and repulsions exist between the diverse ions and proteins in the solution and correlates with a difference in mobility for the different ions and polypeptides through the channel. Thus, density inhomogeneities and re-structuring of the ions/polypeptides in the fluid phase occurs.

FIG. 8A provides a graph of impedance phase (in degrees) versus frequency (Hertz) whereas FIG. 8C provides a graph of impedance magnitude (in Ohms) versus frequency (Hertz). Approximate nanochannel dimensions were about 100 nm×600 nm×2.5 cm. The number of channels was about 5×10⁴. The equivalent circuit used for modeling of EIS data collected in the presence of nanochannels is shown as an insert in FIG. 8B.

FIGS. 10A and 10B are block representations of a nanofluidic switching analogue to field effect transistor (FET). The independent gate bias applied to the electrode below the nanochannels controls the electric double layer and therefore the flow.

DETAILED DESCRIPTION OF THE INVENTION

Figure 1A:
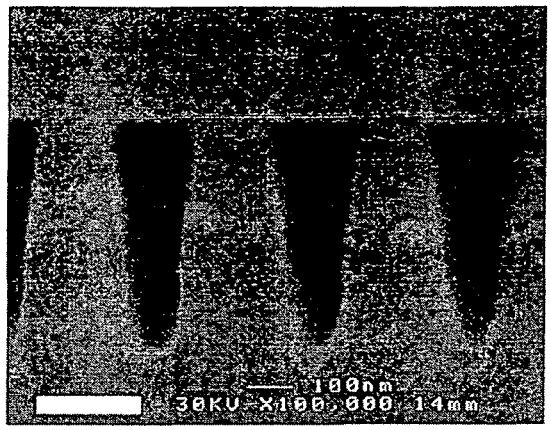
FIG. 1A provides a scanning electron microscopic (SEM) image of a nanochannel array according to one example of an embodiment of the invention.

The invention provides nanochannel devices for separation and analysis of molecules, including complex biomolecules. In one embodiment, the nanochannel device of the invention has one or more nanochannels in a substrate where the nanochannel device is adapted to form a gradient of channel size, ionic charge, electrical current or a combination thereof along the nanochannels. Thus, in one embodiment, a nanochannel can have one or more isolated electrically conductive elements along its length where voltage can be applied to modify the electrical potential along the length of the nanochannel. In another embodiment, the nanochannel is adapted either chemically or electrically to generate or modify a pH gradient along the length of the nanochannel.

The device generally permits transport of fluid flow through the nanochannels. Any and all fluids can be used to transportions, molecules and biomolecules through the nanochannels of the present devices. Fluids used to move ions, molecules and biomolecules through the nanochannels include liquids and gases. In some embodiments, the fluid is an aqueous solution. Fluid movement through the nanochannels can be facilitated by application of voltage (i.e. by generating an electrical current), or by use of hydrostatic pressure, or by capillary action.

As contemplated herein, the nanochannel devices of the invention can be used to separate molecules by charge, size and/or a combination of charge and size.

DEFINITIONS

The "Debye length" as used herein, is the distance over which an individual charged particle can exert an effect. An electric field of an isolated charged particle diminishes as the square of the distance from the particle. In electrolyte solutions (or plasma), however, this field is modified by additional screening due to other charges that randomly move due to thermal motion. The field of each charged particle is thus partially shielded by its immediate neighbors and decrease exponentially with separation distance (exp(-kx)). The distance $k^{-1}$, is called the Debeye length, and is an approximate measure of the distance over which an individual charged particle can exert an effect. For practical purposes, volumes greater in radius than a Debye length are considered to be approximately neutral (although, strictly speaking, the potential is nonzero and continuing to decrease exponentially beyond it). The Debye length is equal to (6.9 times the square root of (T/n)) in centimeters, where T is the temperature of the electrolyte solution (or plasma) in degrees Kelvin and n is the number of ions per cubic centimeter.

A "double layer" as used herein refers to two layers of charge formed (1) by a charged surface and (2) by ions in solution that are attracted to that surface. In the context of the present invention, the nanochannel walls can be electrically or chemically charged while attracted ions that approach the surface of the charged nanochannel walls can form a layer balancing the charge of the wall. The ions in solution can move throughout the solution so that their electrostatic interactions are in competition with Brownian motion. The distance over which the ions in solution form an ionic gradient represents a potential drop within the diffuse layer of ions. The overall result is two layers of charge (the double layer) and a potential drop.

A "double layer overlap" as used herein means that double layers formed on two sides of a nanochannel overlap. Thus, the potential drop within the diffuse layer of ions near one wall of a nanochannel can overlap with the potential drop within the diffuse layer of ions near the opposite wall of the nanochannel.

A "fluid" as used herein is a liquid or gas that can flow through a nanochannel of the invention. In some embodiments, the fluid is a liquid. Fluids that can be used include, for example, water, buffered aqueous solutions, alcohol solutions, organic solvents, nitrogen, argon, and the like. In some embodiments, the fluid is an aqueous solution.

Nanochannel Devices

The invention includes a nanochannel device that includes at least one nanochannel through which a fluid can move, wherein an ionic double layer forms in the fluid near each wall of the nanochannel and an ionic double layer formed along one wall of the nanochannel substantially overlaps an ionic double layer formed along an opposing wall of the nanochannel; and wherein a first electrical potential difference can be applied to the fluid at the ends of the nanochannel to induce electrokinetic transport along the nanochannel. Substantial overlap is overlap of at least about 1%. In other embodiments, substantial overlap is overlap of at least about 5% or at least about 10%. Thus, an ionic double layer generated by ionic interactions along one wall overlaps with an ionic double layer generated by ionic interactions along an opposite wall. As described herein, such substantial overlap cannot occur when the opposing walls of a channel are too far apart. For example, little or no ionic double layer overlap occurs when channel walls are greater than about 1000 nm apart, and in some embodiments when channel walls greater than about 750 nm apart, or greater than about 500 nm apart.

In some embodiments, a second electrical potential difference can be applied between at least a segment of a nanochannel wall and the fluid at one end of the nanochannel to modify the electrostatic potential distribution within the nanochannel and thereby modify the movement of ions and molecules through the nanochannel.

A portion of one wall of the nanochannel can be multilayered with an electrically conducting layer, which can be connected to the second electrical potential. Such an electrically conducting layer can be a semi-conductor or a metal. In some embodiments, the electrically conducting layer is silicon on insulator. In further embodiments, an insulating or selectively conducting layer is interposed between the electrically conducting layer and the fluid within the nanochannel. Such a selectively conducting layer has at least a 10-fold difference in conductivity relative to the electrically conducting layer. In some embodiments, a selectively conducting layer has at least a 100-fold, or a 1000-fold, or a 10,000, or even a 100,000 difference in conductivity relative to the electrically conducting layer. In further embodiments, a selectively conducting layer has at least a $10^6$ difference in conductivity relative to the electrically conducting layer.

An electrical voltage can be applied to the nanochannel to modify an electrostatic potential in the nanochannel and thereby control movement of ions, molecules and biomolecules through the nanochannel.

Figure 16:
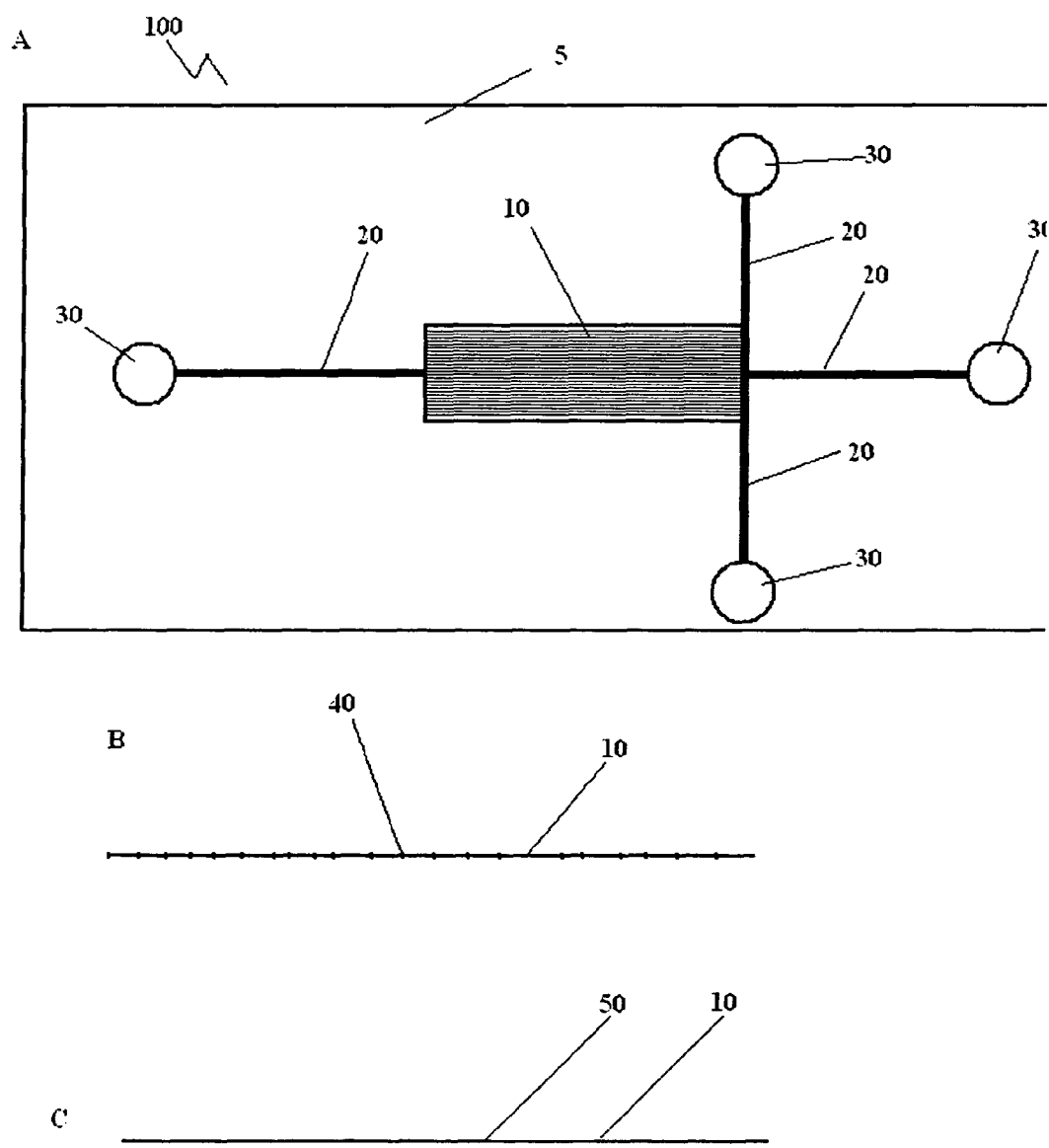
FIG. 16A is a schematic diagram of one example of a nanochannel device of the invention.
FIG. 16B is a schematic diagram illustrating one type of nanochannel that can be present in the devices of the invention. The channel (10) can have one or more, in some embodiments a series of, electrodes (40) at regular or irregular intervals along the nanochannel (10).
FIG. 16C is a schematic diagram illustrating another type of nanochannel that can be present in the devices of the invention. Electrophoresis through a nanochannel (10) can be achieved by application of electrical current (50) through the nanochannel. For example, an electrical current can be applied at well or port connected to a nanochannel through a microchannel.

One example of a device of the invention is provided in FIG. 16A. The device (100) has a substrate (5) and one or more nanochannels (10). One or more microchannels (20) can also be included in the device (100) and selected microchannels (20) are coupled to the nanochannels (10). Microchannels (20) can be used to supply fluid and/or samples to the nanochannels (10). One or more wells (30) can be included to provide fluid to the microchannels (20) or the nanochannels (10). An electrical source can be connected to fluid in at least two wells (30) to generate a difference in potential between ends of the microchannels (20) and/or the nanochannels (10) to facilitate movement of ions and molecules through the nanochannels (10).

FIG. 16B provides a schematic diagram of a nanochannel (10) that can have one or more electrodes (40) along the nanochannel (10). One or more electrodes (40) can be present at regular or irregular intervals along the nanochannel (10) so that an electrical voltage can be applied to modify the electrical potential along the nanochannel. In addition in some embodiments, an electrical current (50) can flow through one or more nanochannels (10). In one embodiment, multiple electrical potential difference sources are connected between multiple electrically isolated portions of the nanochannel wall and the fluid at one end of the nanochannel to modify the electrostatic potential.

Nanochannels in the devices of the invention may have a width of about 1 nm to about 1000 nm, or about 10 nm to about 500 nm, or about 15 nm to about 100 nm. The width of the nanochannels can also vary from one end of a nanochannel to the other. For example, the width can be about 10 nm at one end of the nanochannel and about 1000 nm at the other end. In other embodiments, the width can be about 10 nm at one end and about 100 nm at the other.

The nanochannels often have a width that is less than their depth, but in some embodiments the width can be about the same or even greater than their depth. For example, nanochannels can be about 10 nm to about 2 μm deep, or about 200 nm to 1.5 μm deep or about 500 nm to about 1000 nm deep. The nanochannels in the devices of the invention can be about 50 nm to about 10 cm long. Nanochannels that have been successfully and routinely used were about 40 nm wide by 1 μm deep, by about 1 cm long (see, e.g., FIG. 2A). A depth of about 0.5 micrometers to about 2 micrometers facilitates detection of molecules that are being separated and helps to eliminate the effects of the bottom of the nanochannel, which with such deep nanochannels will not affect molecular separation so significantly.

In some embodiments, the nanochannels in the substrate are connected to microchannels having a larger width, depth or diameter (e.g. about 1 micron to about 300 microns) than the nanochannels. Such microchannels can supply the nanochannels with fluids, electrolytes, pH gradients, and electrical potentals. Various embodiments of the invention can also include wells in the substrate to further supply fluids, ions, pH gradients and electrical currents. The wells can be placed to facilitate application of an electrical potential source. For example, wells can be joined to microchannels or nanochannels that intersect nanochannels to thereby form tee-junctions (see, e.g., FIG. 16A). Thus, several wells can be present on or in the devices of the invention.

The nanochannel devices of the invention can have a cover on or over the nanochannel. Such a cover can, for example, include an insulating material. Example of cover materials that can be used also include glass, Pyrex, silicon or germanium.

In addition, the devices of the invention can include electrodes, drains, tubing for fluid input, and detectors for identifying and detecting molecules and biomolecules separated by use of the devices of the invention. Such detectors can provide feedback through linkage to electrical components that can modulate the electrical potential within and flow rate along the nanochannel(s). Moreover, such detectors can provide feedback to switches that can shunt the flow of one or more molecular species into a different nanochannel or through a series of different nanochannels.

The invention also includes arrays and networks of the nanochannels or nanochannel devices described herein. Thus, in some embodiments, the invention is directed to arrays of about 2 to about 10,000 nanochannels, or about 10 to about $10^8$ nanochannels. In other embodiments, at least one nanochannel device is joined to at least one other nanochannel device. In other embodiments, the invention is directed to a series of nanochannel devices where the nanochannels can be connected in series, run parallel to each other or interconnect with each other as desired by one of skill in the art. In still other embodiments, the invention is directed to layers of nanochannel devices that can be interconnected at selected intervals, that can operate synchronously or that can operate largely independently of each other.

As shown in FIG. 16A, the transverse extent of the array of nanochannels may be wider than the microchannel. To couple the array of nanochannels with a microchannel, the microchannel may be widened in the vicinity of the junction with the array of nanochannels to provide fluid to the entire array of nanochannels. Alternatively, a chamber may be formed between the nanochannels and a microchannel to provide a fluidic interface. The chamber may be designed to facilitate flow of the fluid between the nanochannels and the microchannel.

The invention includes integrated networks of nanochannels that can include electrodes, interconnecting channels (microchannels or nanochannels), drains, tubing, ports or wells for fluid input, detectors for identifying and detecting molecules and biomolecules, and the like. The networks can include switches for directing fluid from a nanochannel into a detector, microchannel, well, drain or into a different nanochannel. Such networks can be generated as a single unit, for example, in a single substrate, or in several or many units, in a number of separate substrates.

Thus, the invention provides a network that includes multiple devices of the invention. Such a network can include electronic components that control the first and/or second electrical potential differences applied to each device, and multiple detectors for observing ionic or molecular transport within each device. Thus the network including multiple devices, can also include electronic components that control the first and second electrical potential differences applied to each of the devices, and multiple detectors for observing ionic or molecular transport within each device, wherein the electronic components are interconnected with the detectors to adjust the first and second potential differences in response to the observed ionic or molecular transport within each device.

The substrate used for forming the nanochannel devices of the invention is generally comprised of materials such as silicon, silicon oxide, germanium, germanium oxide or a suitable polymer material (e.g., poly(dimethyl siloxane)). However, the devices of the invention can be multi-layered with one or layers of such materials, or with added layers of electrically conductive materials, electrically non-conductive materials or electrically semi-conductive materials. Metals, phosphorus atoms and other elements, impurities or materials can be introduced, for example, by doping, to alter the resistance of the substrate at selected locations.

The surface of the nanochannels in the substrate can be sealed with silicon oxide (e.g. $SiO_2$) or germanium oxide (e.g. $GeO_2$). Such an oxidized layer can be generated thermally or by plasma-enhanced chemical vapor deposition to thereby line the nanochannel walls with a thin layer of hydrophilic material. The amount of oxidation can be varied to modify the width of nanochannels—greater oxidation can lead to narrower nanochannels. Alternatively, a thick layer of silicon oxide can be generated on a silicon substrate and the nanochannels and other features can be etched into the silicon oxide, to generate nanochannels and other features within the silicon oxide. In some embodiments, the silicon oxide is etched to generate nanochannels and/or other features that comprise essentially silicon along their walls.

Figure 1B:
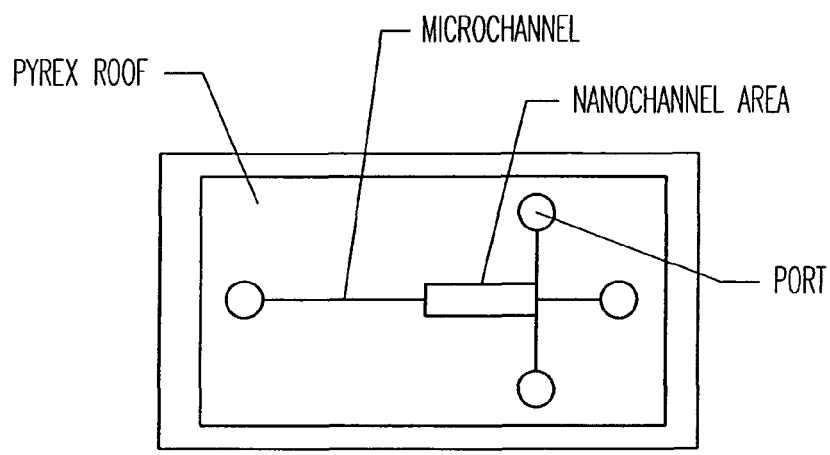
FIG. 1B provides a schematic diagram of an integrated chip device of the invention with nanochannel area, microfluidic channels, and macroscopic ports or wells. Note that the highlighted nanochannel area connects to macroscopic ports by microfluidic channels according to one example of an embodiment of the invention.
Figure 1C:
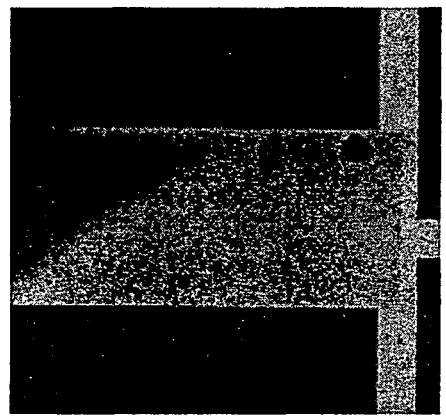
FIG. 1C provides a confocal image of dye flow in an integrated device of one embodiment of the invention. The dashed box highlights a plug of dye in the nanochannel area.

The "T-chip" shown in FIG. 1 illustrates one embodiment of the invention. This T-chip has a nanochannel area with numerous nanochannels, several microfluidic channels, and macroscopic wells or ports. Note that the highlighted nanochannel area connects to macroscopic ports by microfluidic channels.

The T-chip of FIG. 1 provides several benefits, including the following: (1) reproducible production, (2) probing of the fluid in the nanochannels or microchannels by a range of spectroscopic techniques (e.g., fluorescence, Raman, and infrared), (3) detailed examination and control of the electrostatic and electrokinetic phenomena that govern flow through the nanochannels, and (4) controlled introduction of sample plugs (bands) of molecular mixtures into the nanochannels. Thus, the devices of the invention can be used to monitor the mass transport of biomolecules, including proteins, protein complexes, nucleic acids (DNA and RNA), subcellular organelles, viruses, phage, and the like in the nanochannels.

Figure 8A:
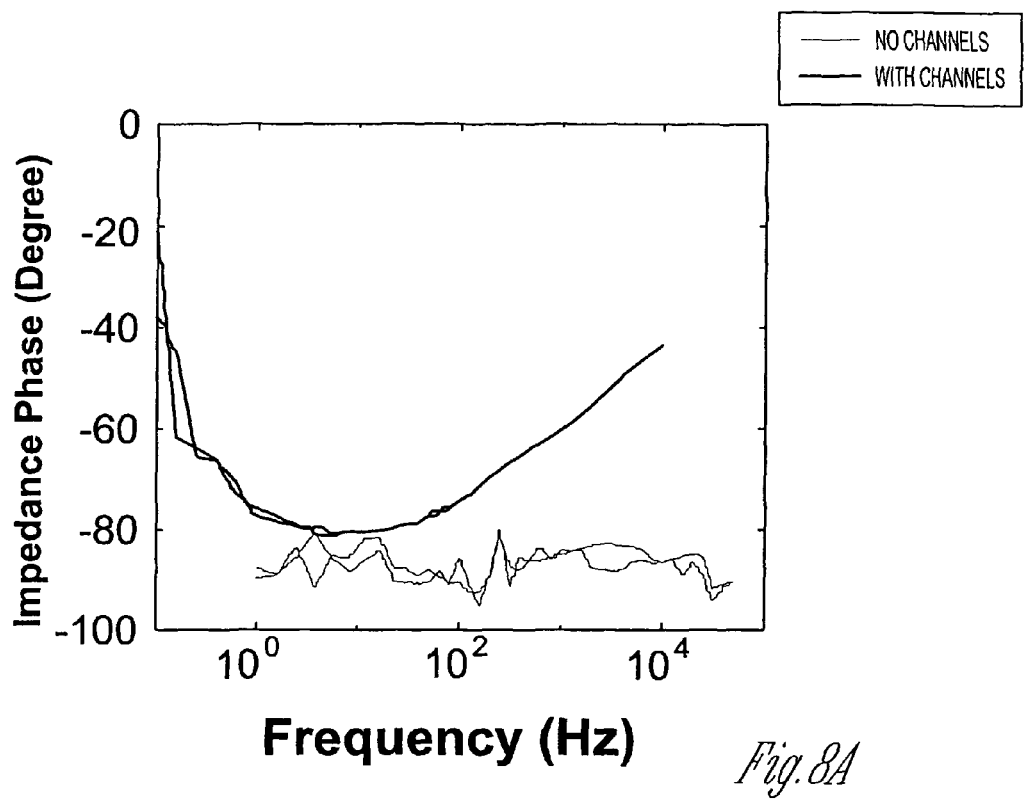
FIG. 8A-C are bode diagrams from electrochemical impedance spectroscopy (EIS) of chips with and without a nanochannel array.
Figure 8B:
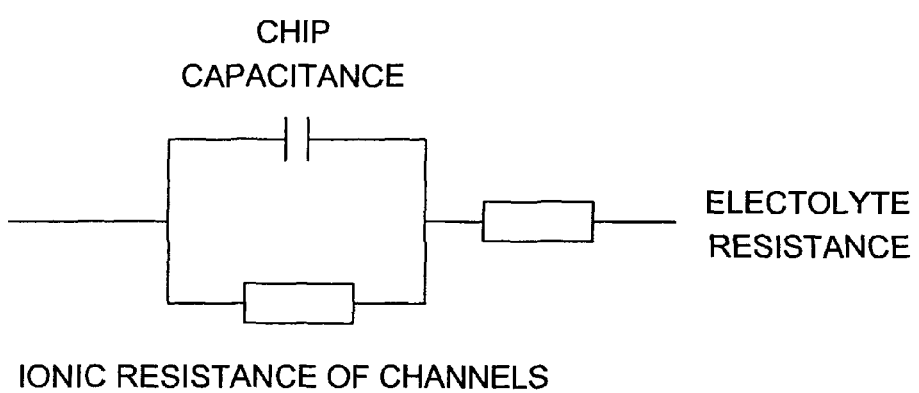
Figure 8C:
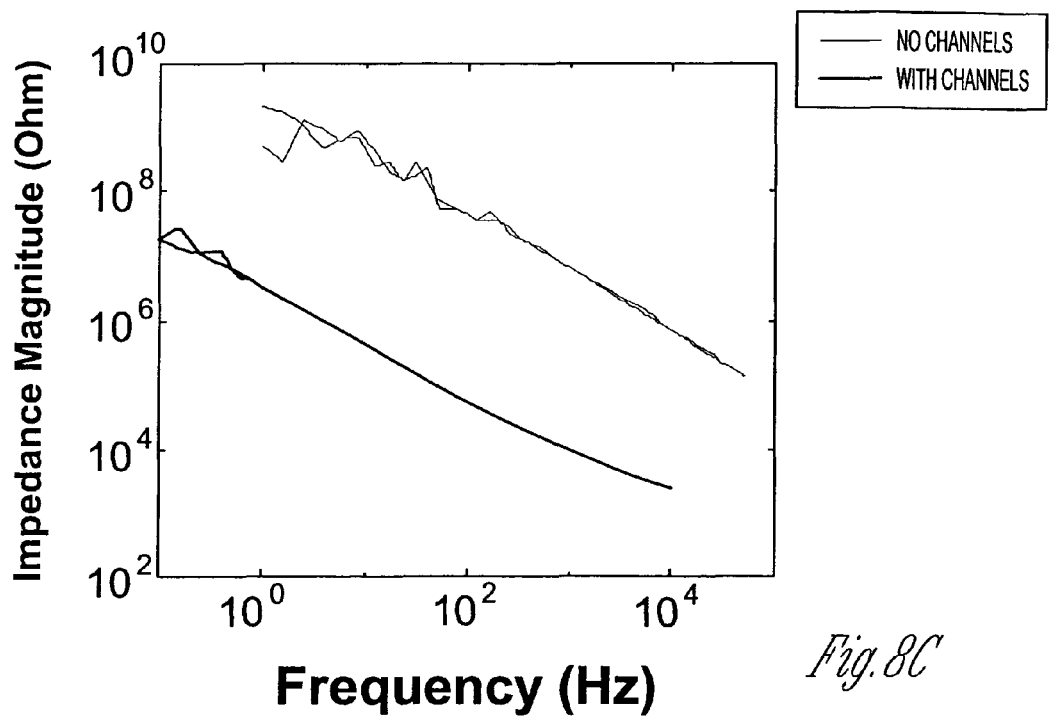

Detection of ions, molecules, and biomolecules in the nanochannels can be by fluorescence spectroscopy (see, e.g., FIG. 1C), infrared (IR) spectroscopy, electrochemical impedance spectroscopy (EIS, see, e.g. FIG. 8A-C), ultraviolet spectroscopy, confocal microscopy, and the like. Moreover, detecting separation of molecules can involve use of detectable label, e.g. a spectroscopically detectable leabel. In some embodiments, a color intensity profile can be observed and software can be used to determine the presence or concentration of a labeled molecular species.

Figure 2A:
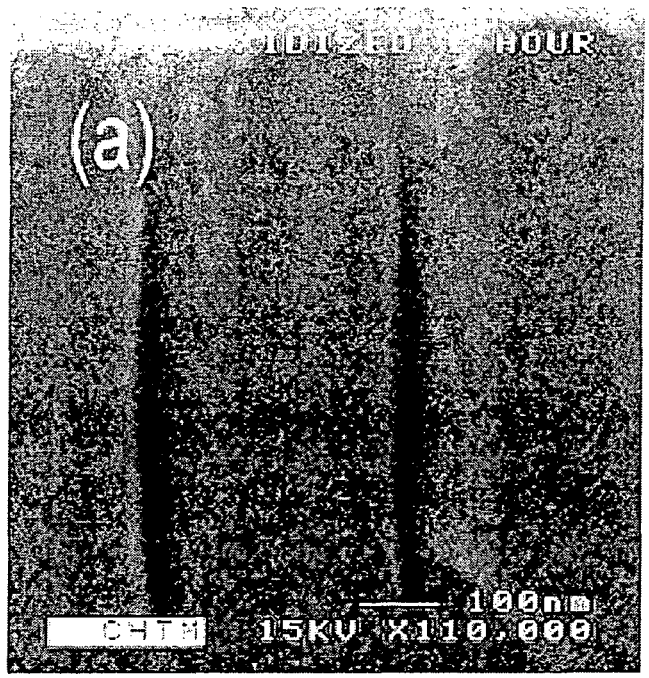
FIG. 2A-B provide SEM images of nanochannels with widths of less than 100 nm, where the nanochannels were generated in oxidized silicon.
Figure 2B:
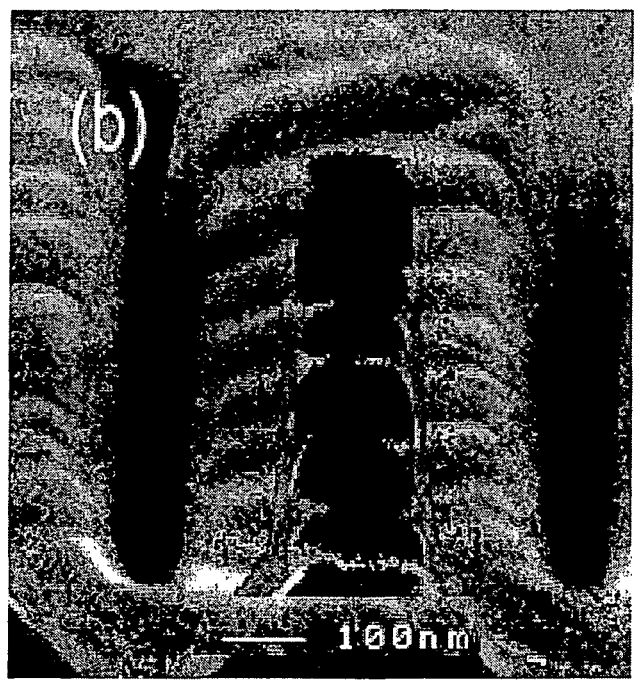

Adding to the T-chip's versatility, FIG. 2A illustrates the level of anisotropy that can be introduced to the nanochannels. The depth and width for these channels were 700 nm and less than 50 nm, respectively. The thermal oxidation of etched silicon channels resulted in trench widths of less than 50 nm. FIG. 2B reveals the remaining silicon wall after removing the oxide layer with a hydrogen fluoride solution. The silicon wall image in FIG. 2B is superimposed on top of the original oxidized channel image to demonstrate the level of oxidation. This result indicates that the remaining silicon can be further oxidized to create even narrower channels.

Figure 3A:
FIG. 3A-B provides an example of contiguous, tapering photoresist bands that can be used to create gradients in the width of nanochannels.
Figure 3B:
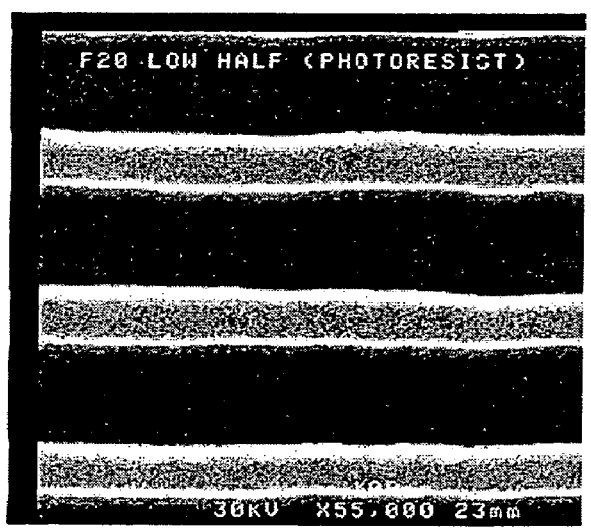
Figure 4:
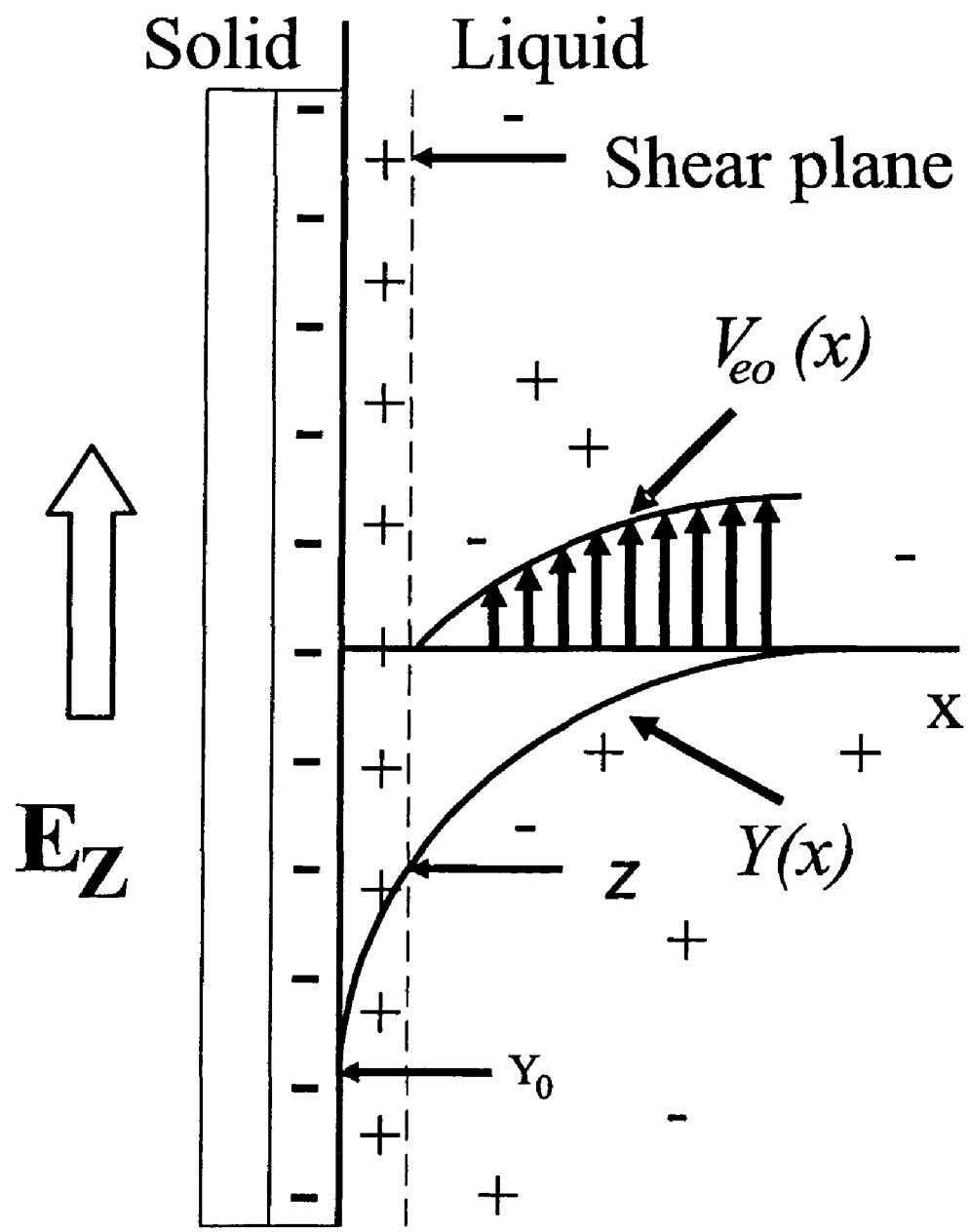
FIG. 4 provides a schematic representation of a solid-fluid interface and the origin of electroosmosis. As shown in this diagram, the dark solid surface is negatively charged, creating an unequal distribution of charge in the fluid phase. Positively charged ions are attracted to the negatively charged solid surface, creating a potential $\psi(x)$ at the solid-fluid interface. The magnitude of this potential decays with increasing distance (x) from the solid wall according to the formula: $\psi(x) = \psi_0 \exp(-\kappa x)$, where parameter $\kappa^{-1}$ is the Debye screening length associated with the thickness of the electrical double layer. As further described herein, the electrical potential gradient facilitates separation of complex mixtures of biomolecules as they travel through the nanochannel devices of the invention. Such an electrical potential between the walls of the nanochannels and the fluid in the channels can only be properly maintained when the channels are nanochannels because the electrical potential decays exponentially with distance from the channel walls.

The nanochannels of the present devices can include a gradient of diameters or sizes. Such size gradients can be generated by exposing different areas of the photoresist for different durations using interferometric lithography as described herein. FIG. 3A-B provides an example of contiguous, tapering photoresist bands to create gradients in the sizes/diameters of nanochannels.

Double Layer Overlaps and Fluid Inhomogeneities Affect Nanochannel Electro-Osmosis Electro-osmosis (EO) can move fluid through capillaries, microchannels and nanochannels. Electro-osmotic flow can be generated when a solid wall comes into contact with an electrolyte solution. An electropotential having the following formula develops at the interface (R. J. Hunter, *Zeta Potential in Colloid Science*. (Academic Press, New York, 1981)).

$$\Psi(x) = \frac{4}{z}\operatorname{arctanh}\left[\tanh\left(\frac{z\Psi_0}{4}\right)\exp(-\kappa x)\right], \Psi = \frac{e\Psi}{kT} \quad (1)$$

The magnitude of this potential decays with increasing distance from the wall, and the important parameter $\kappa^{-1}$ (Debye screening length) is associated with the thickness of the electrical double layer. The potential gradient leads to accumulation of counterions in the vicinity of the solid-fluid interface. In an externally applied longitudinal electric field, $E_z$, these counterions start moving, thus transmitting their momentum to the surrounding fluid. The counterions in the closest layer to the surface, however, are immobile due to the strong electrostatic force that keeps them in place. The fluid motion starts at the shear plane, and a velocity profile v(x) develops. The potential at the shear plane is an important parameter in the analysis of electrokinetic data and is called the zeta-potential ($\zeta$).

For double layer thicknesses that are much smaller than the capillary diameter, one may ignore the detailed shape of the fluid velocity distribution at the interface and assume a plug flow across the channel (see FIG. 5A). In this case and assuming also that the dielectric permittivity is constant across the channel, the bulk fluid velocity is given by the Smoluchowski expression below.

$$V_\infty = v(x \to \infty) = -\frac{\varepsilon \varepsilon_0 \zeta E}{\eta} \quad (2)$$

where $\varepsilon\varepsilon_0$ is the fluid dielectric permittivity, $\eta$ is the viscosity, and E is the applied electric field. It is also evident that the electro-osmotic velocity depends linearly on the electropotential ($\zeta$) of the channel walls.

The situation becomes much more complicated when the double layers overlap. When the double layers overlap, the fluid velocity profile follows the shape of the potential distribution in the channel (see FIG. 5B). For a cylindrical capillary with radius, R, with overlapping (thick in comparison with R) double layers, the electro-osmotic velocity profile (for small potentials) is given by formula (3).

$$v(r) = -\frac{\varepsilon\varepsilon_0\zeta E}{\eta}\left[1 - \frac{I_0(\kappa r)}{I_0(\kappa R)}\right] \quad (3)$$

where $I_0$ is a Bessel function of order zero. Clearly for $\kappa R \gg 1$ this equation reduces to the Smoluchowski expression above.

These analyses are valid when the fluid is a structureless continuum, and this is a valid assumption for most practical situations. When the channel width is reduced to nanoscale sizes, however, the approximation that the fluid is a structureless continuum breaks, particularly in the case of protein (or other biomolecular) solution flow. In the nanochannels of the invention the inhomogeneities in the fluid structure should be considered (see FIG. 6). Several different types of structuring of varying length scales exist during nanoscale separation. First, the solvent is not structureless but is instead composed of individual solvent molecules, which are a few Ångstroms in size, and which interact with one another. Second, electrolytes and hydrated ions, which are about a few nanometers in size, are present in substantially all biomolecular solutions. Ions tend to hydrate, binding water molecules and also interact with one another by long-range coulombic forces. Biomolecules such as proteins and nucleic acids are often about 10 to about 50 nanometers in size, and are much larger than solvent molecules and hydrated ions. Biomolecules also hydrate and exhibit interactions. All of these interactions and molecular/ionic size constraints lead to inhomogeneities in the solution that range from about a few nanometers to a few tens of nanometers.

At low electrolyte concentrations, the double layers around the molecules and in the vicinity of the nanochannel walls further enhances the structuring and leads to solution inhomogeneities. These inhomogeneities within the nanochannels of the invention contribute to the forces that operate to separate one type of biomolecule from another, and from the ions and other small molecules associated with that biomolecule.

The problem of flows of inhomogeneous fluids in narrow channels has been studied in the past. However, these studies involved ideal systems such as ensembles of hard spheres interacting with a model Lennard-Jones potential. More elaborate theoretical approaches are needed to model, analyze, and optimize the transport of real protein solutions in nanochannels.

As a first step in the theoretical analysis, the interactions and correlations between dissolved biomolecules (e.g. proteins) and the nanochannel walls are considered, while the solvent together with the low molecular weight electrolyte will be considered as a structureless fluid. The effect of the electrolyte solution on the biomolecule-wall can be accounted for by the dielectric permittivity, $\varepsilon$, of the solvent and the screening parameter, $\kappa$, which depends on the concentration of background electrolyte, $C_{el}$, as follows.

$$\kappa = \frac{(2e^2z^2C_{el})^{1/2}}{(\varepsilon\varepsilon_0 kT)^{1/2}} \quad (4)$$

where e is the unit charge, z is the electrolyte valency, and kT is the thermal energy. This semi-continual approach cannot always be solved by simple mathematical analysis, thus analytical software such as the FEMLAB package can be used to model particular cases.

Another step in a theoretical description of flows in nanochannels includes molecular dynamics simulations. This approach will take into account every single molecular component in the system explicitly. Although the problem is very complex, there are some initial attempts to simulate electrolyte solutions and their electro-osmotic transport in microchannels. Algorithms for doing such non-equilibrium molecular dynamics simulations have been developed. See, Bitsanis et al. J. Chem. Phys. 89: 3152-62 (1988); Pozhar & Gibbons, Phys. Rev. E. 56: 5367-96 (1997); Travis & Gibbons, J. Chem. Phys. 112: 1984-94 (2000); Travis et al., Phys. Rev. 55: 4288-95 (1997); Thompson, J. Chem. Phys. 119: 7503-11 (2003). These algorithms generate the fluid velocity profile in extremely narrow channels and pores along with the components of the stress tensor. The new features to be simulated and accounted for in these algorithms are (i) the presence of nanometer sized biomolecules in the flowing solution and (ii) the small nanometer size of the channels.

The third theoretical approach that can be considered for analyzing nanochannel separation is based on the Boltzmann kinetic equation.

$$\frac{\partial f}{\partial t} + v\nabla f = J_{coll} \quad (5)$$

Solving this equation gives a non-equilibrium distribution function $f(\tau,v,t)$ for each molecular species in the system and the transport properties of the fluid. $J_{coll}$ is the collision integral. Knowing the distribution function, the statistically averaged quantities, such as the velocity of each molecular species, can be calculated. Some attempts to use kinetic equations to model flows of inhomogeneous fluids have been made in the past. See, Pozhar & Gibbon, J. Chem. Phys. 99: 8970-96 (1993). The advantage of this approach, compared with molecular dynamics simulations, is that often it requires less computational resources and therefore allows for modeling more complicated systems. Its disadvantage, however, is that it introduces some approximations related to the collision term in the Boltzmann equation. Therefore, different theoretical analyses can help in proper interpretation and modeling of different separation phenomena.

Nanofluidic Separation

At the nanoscale, molecular and surface interactions dominate transport. Two simple examples serve to illustrate the physical processes that come into play. The electrical double layers that arise from electrolyte screening of the ionic surface charges on nanochannel walls, $L_{Debye}$, are about 3 Ångstroms to about 300 nm wide in aqueous solutions. These double layer widths are comparable to the nanochannel widths of the present invention, $W_{chan}$, and are also comparable to the size of some dissolved macromolecules, $L_{mol}$. For example, the nanochannels often generated for routine experimentation are about 40 nm wide by about 1 µm deep, by about 1 cm long (FIG. 2A). The channels are often formed by etching of silicon and oxidation to form an insulating layer between the silicon and the fluid as described herein.

An external voltage can be applied between the silicon substrate (e.g., the nanochannel walls) and the fluid to control the ζpotential at the fluid surface, and thereby control the electroosmotic flow of solutes through the nanochannels. Further description of such electroosmotic forces is available, for example, in Minagawa et al. J. Colloid Interface Sci. 188: 176-82 (1997); Ramirez et al., J. Electroanal. Chem. 436: 119-125 (1997). However, the devices of the invention differ in significant ways from previous work, including the work of Managawa et al. and Ramirez et al., in several respects. First, the devices of the invention have a three order-of-magnitude reduction in channel width compared to previously generated channels. Thus, previously available channels had a width of about 25 µm compared to the present nanochannels that routinely are made with widths of about 20-50 nm. Second, an overlapping double layer evolving from both sides of the present nanochannels is achieved as opposed to a single double layer on an electrode side with previously available channel devices. Third, the present nanochannel devices can employ a reduced thickness gate oxide (of about 100 nm) allowing higher fields and a more direct coupling between the gate voltage and the fluid potential. Significantly, the fabrication technology of the present invention is scalable and amenable to the fabrication of large numbers of nanochannels on a single device or chip, enabling production of a nanofluidic separation architecture with much greater functionality than that of a single macroscopic device.

The fluid transport properties of nanochannels can be controlled by adjusting the electrical potential of the nanochannel walls. This is roughly analogous to the control of current in a field-effect transistor (FET). Just as in the electronic case, the provision of a gate electrode that surrounds the channel provides substantially more control than does a single sided electrode (for example, from the top of the channel). See, e.g., Ramirez et al. J. Membr. Sci. 161: 143-55 (1999); Jimbo et al. J. Colloid Interface Sci. 225: 447-54 (2000). Such control permits development of a nanofluidic circuit with the same advantages of complexity and distributed intelligence that transistors and integrated circuits have brought to information processing.

The fluid transport properties of nanochannels can also be controlled by adjusting the surface charge density on the nanochannel wall. This can be done chemically (as well as electrically). For example, the surface charge density of a nanochannel can be chemically adjusted by introducing protonating or deprotonating agents, or by introducing acids or bases into the nanochannel. In other embodiments, the nanochannel wall surface charge density can be chemically adjusted by introducing protons, hydroxyl ions, amines, ammonium ions, formic acid, metallic ions (e.g. barium) or larger charged polymers. For example, the nanochannel wall surface charge density can be chemically adjusted by introducing polylysine or a polyelectrolyte. Such a polyelectrolyte includes one or more polymers that can be charged positively or negatively. In some embodiments, a polyelectrolyte is compounded from two or more polymers, some of which may be positively charged while the other(s) is/are negatively charged.

Moreover, because large proteins and other biological species such as DNA are of the same dimensional scale as the nanochannels, new transport phenomena are involved. For example, it is known that DNA fragments must unravel to enter nanochannels, but such linearization of nucleic acids during separation has previously not been exploited as a mechanism for separation and analysis of the nucleic acids.

The analogy between a transistor (electron or hole charge transport between source and drain mediated by a gate voltage) and a nanofluidic switch (charged species transport through a fluid mediated by a gate voltage) is illustrated in FIG. 10. In an electronic transistor the conductivity of a narrow channel between the source and drain contacts is controlled by the potential applied to a gate electrode that is isolated from the electron channel by a thin oxide layer. In the fluid devices of the invention, transport of charged molecular species between the microchannel regions on either side of the nanochannel regions is modulated by the potential applied to an electrode separated from the fluid flow by a thin oxide. The gate electrode of the present nanochannel devices can be the bulk silicon substrate itself or isolated and individually addressable electrodes.

Moreover, control of the electroosmotic flow of biomolecules is similar to control of electric flow in transistors. Such control is achieved in both cases by manipulation of the local potential through accumulation and depletion of charged carriers at the interface. In the transistor case, the language used is the manipulation of Fermi levels and conductivity of the channel. In the fluid case, the language used is the double layer and the infusion/expulsion of charge carriers in response to the applied field. In both cases, the channel width has to be within the accessible spatial scale of the modulation. For the fluid case, this is only available at nanoscale dimensions, comparable to the thickness of the double layer. Hence, microscale channel devices do not perform the same way that nanoscale channel devices perform; nor is biomolecular separation controlled in microscale channel devices as readily as in nanoscale channel devices.

As explained above, the double layer arises from charge screening. There is a fixed charge on the channel wall interface (generated, for example, by oxidation) while the charged ions/molecules in the fluid adjust to screen those charges from the bulk of the fluid. This concept was introduced by Debye and Hückel almost a hundred years ago. The screening length is given by Equation 4, above.

By biasing the gate electrode the skilled artisan can swing the ζ-potential over wide ranges and, in particular, can set the electro-osmotic flow to precisely cancel the electrophoretic flow for a particular biomolecular species, thereby offering an electronic switch. This is a fundamentally new capability, because existing switches in microfluidics depend on mechanical motion, for example, squeezing on an elastomer to shut off a channel. Electronic control in the present nanochannel devices is faster, more reproducible, and offers much greater finesse for the control of the channel flow characteristics and movement of individual biomolecular species. Moreover, with an additional layer of logic, the gate region under each array of nanochannels can be individually addressed, offering an electronically addressable flow capability.

The capability of controlling flow and modulating flow rate differences between different biomolecular species in nanochannels is an exciting new feature offered by the nanochannel devices of the invention. The ability to build complex circuits from relatively simple transistor switch building blocks has had revolutionary impact on electronics and information processing. One of skill can apply similar capabilities with the nanofluidic circuits of the invention.

Rapid progress in biomolecular separation can also be achieved because the fabrication of the present nanofluidic devices is inexpensive, rapid and easily adaptable. As described herein, the nanochannel fabrication employs established microelectronics batch fabrication and adds interferometric lithography as a nanoscale patterning technique, thereby providing a wide array of inexpensive (both in time and in effort) and readily available nanochannel devices for rapid progress in separating and analyzing biomolecules.

pH Modulation in Nanochannels and Field Effect Transistor (FET) Analogue

An unusual and powerful property of buffered aqueous solutions in nanochannels is that the pH in the channel can be significantly different from the pH of a bulk solution in contact with that channel. This pH shift can be predicted by extensions to the diffuse double-layer theory discussed above to include hydronium, hydroxy and buffer ions. A qualitative explanation for such pH shifts is that, if the walls of the channel are negatively charged, then positively charged hydronium ions are selectively imbibed into the channel, so the spatially averaged pH consequently decreases. Conversely, a pH increase occurs in the channel when the walls are positively charged.

Figure 11:
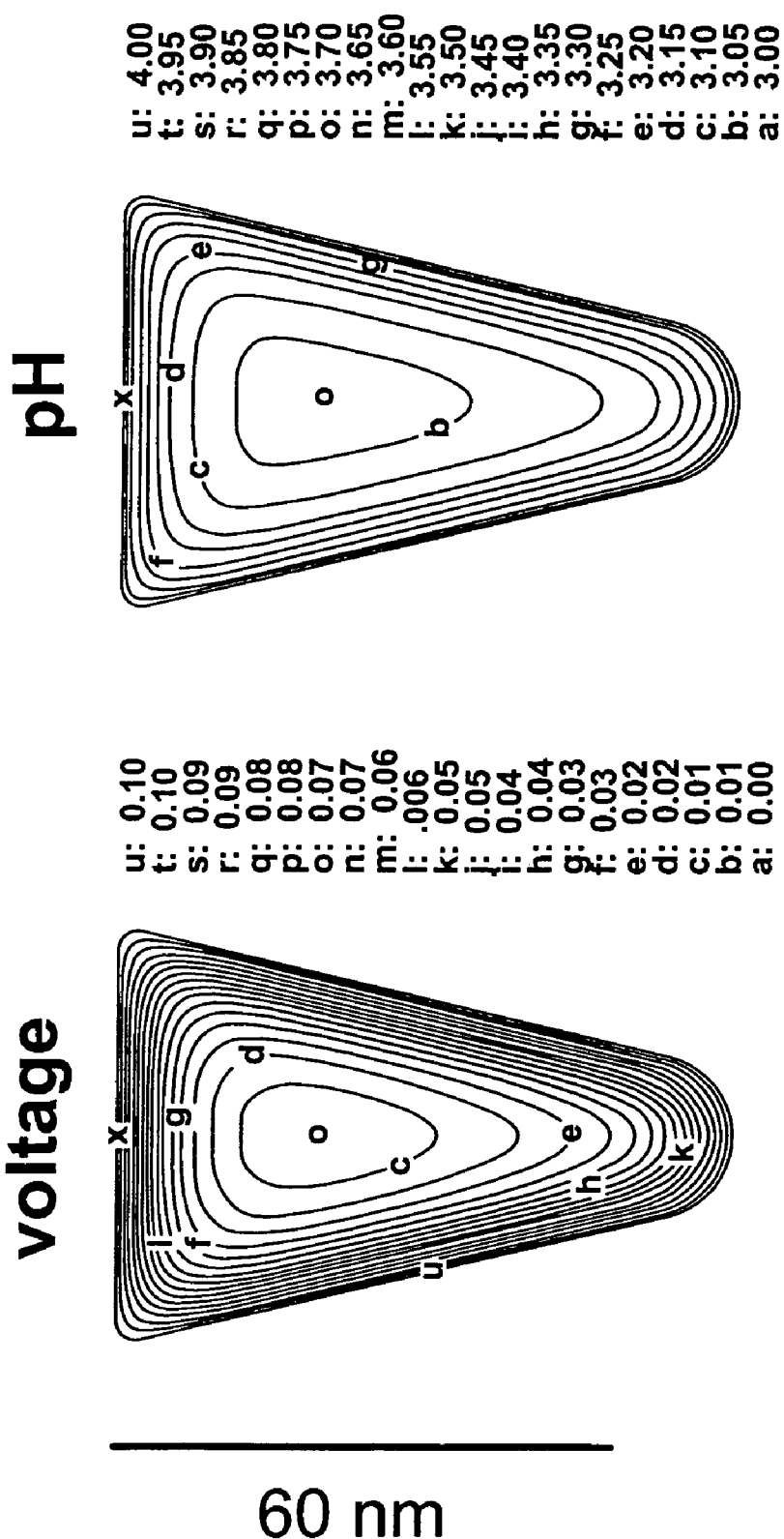
FIG. 11 illustrates pH and voltage contours for a 60 nm channel with a +100 mV ξ-potential exposed to an unbuffered 1 mM NaCl bulk electrolyte solution at pH 8.5. The positive channel wall charge causes the constricted double-layer to imbibe an excess of hydroxyl ions, raising the pH by more than 0.2 units. Note that, even in the center of the channel, the potential has not decayed to zero and the pH has not decayed to the bulk pH.

As the ionic strength of the fluid is reduced, the double-layer extends farther away from the wall, occludes more of the channel cross-section and, at very low ionic strengths, will eventually shift the pH everywhere within the nanochannel. Hartley & Haynes, Anal. Chem. 74: 1249-55 (2002); van Theemsche et al. Electrochim. Acta 48: 3307-12 (2003); Schasfoort et al. Science 286: 942-45 (1999). As shown in FIG. 11, this pH shift is predicted to range from about 0.01 pH units to about 2 pH units, where 0.1 pH shift can be seen in larger, lightly-charged channels with high salt concentrations and about 0.5 pH unit can be seen in small, heavily-charged channels with low salt.

Note that the ±100 mV ζ-potential used in calculating such pH shifts may be excessive for surfaces, which change due to normal dissociation reactions. However, it may be possible to achieve such high potentials at the shear-plane using the FET analogue described below. A simplified version of the theory applied to model the potential inside the channels (FIG. 11) is discussed below in the context of impedance spectroscopy.

The inherent surface charge and concomitant pH shift within the nanochannel can be exploited as the basis for an electrokinetic pump or fixed valve, a crudely selective ionic filter or trap, and/or a single channel in a network of nanochannels in an integrated separations device.

Because the present nanochannel devices are based on silicon (or germanium) as a semiconductor, the pH-shift concept can be taken one step further by fabricating the nanochannels with a 100 nm coating of $SiO_2$ or $GeO_2$ and applying a "gate" voltage to the silicon. See, e.g., Minagawa et al., J. Colloid. Interface Sci. 188: 176-182 (1997). This coating acts as an electrical insulator, has a dielectric strength in the neighborhood of 1 V/nm for thermally grown $SiO_2$, and is readily amenable to surface modification using silane and siloxane chemistries. Silica surfaces can also be modified with silane-based reagents and such modifications can be used to control nonspecific and nonspecific protein adsorption.[54-57] See, e.g., Fu et al. Adv. Mater. 15: 1262-66 (2003); Dolan et al. Nucleic Acids Res. 29: e107 (2001); Lopez et al. Science 260: 647-49 (1993); Buch et al., Electrophoresis 22: 3902-07 (2001).

Thus, if a second electrical potential difference, or "gate" voltage, is applied in the range of ±100 V, to the nanochannel wall (e.g., silicon oxide), the electric field across the $SiO_2$ layer will cause the charge at the $SiO_2$—$H_2O$ interface to change, thereby shifting the ζ-potential. See, e.g., Lee et al. Anal. Chem. 62: 1550-52 (1990); Hayes, Anal. Chem. 71:3793-98 (1999); Huang et al., Anal. Chem. 65: 2887-93 (1993); Wu et al., Anal. Chem. 64: 886-91 (1992); Wu et al., Anal. Chem. 65: 568-71 (1993); Lee et al., J. Chromatogr. 559: 133-140 (1991); Righetti et al., Method Biochem. Anal. 32: 215-78 (1987). As a result, the pH in the nanochannel will shift by up to one-two pH units. This "gate" potential may be applied, removed, or even reversed in much the same way this is done in an integrated circuit, e.g., field effect transistors (FETs).

Furthermore, voltage may be applied to an array of nanochannels, locally or globally, both in space and in time in single or multi-gate configuration. With this concept in place, the pH shift can be modulated at will, so that, for example, pH gradients can be set up for isoelectric focusing without the use of ampholytes or Immobilines® to form a stable gradient and then use the same channel or a nearby channel for isotachophoresis or zone electrophoresis as a second dimension. The nanochannel device architecture described herein will also permit tuning of an ion filter or protein trap or adjustment of an electronic valve during operation. These changes can be made discretely or uniformly throughout an integrated network of nanochannels.

Making Nanochannel Devices

Advanced lithographic technique such as interferometric lithography (IL) can be used to producing nanochannels, patterns of nanochannels and similar structures in the devices of the invention. Such nanochannels and related structures may be rapidly created over wide, macroscopic areas at low cost (compared to other techniques such as electron beam lithography). In addition, it may be used to easily generate arrays of nanostructures (protrusions or channels) whose dimensions vary semi-continuously in the plane of surface of the substrate being patterned. IL has advantages over other methods that might be used to construct nanopatterned fluidic structures (e.g., electron beam lithography, X-ray lithography, or local probe lithography) due to the low cost of implementation and the parallel nature of the lithographic technique. Combining IL with conventional lithography allows for the formation of device structures in individual areas and adding periodic features such as transistors, electronic and fluidic connections. Imaging interferometric lithography extends optics to fundamental, deep-sub-wavelength scales.

For the purposes of the present invention, the term "interferometric lithography" (IL) refers to a process of lithography that involves interference patterns of two (or more) mutually coherent light waves. The angles between the light propagation vectors of the waves are sufficiently large to produce an interference pattern that has a high spatial frequency. The resulting interference pattern may have nanoscale dimensions. Examples of interferometric lithography techniques that may be used in the present invention are described in Chen X L, Brueck S R J, "Imaging interferometric lithography: approaching the limits of optics" in Optics Letters, 24, pp. 124-126 (1999), in "Imaging interferometric lithography:

A wavelength division multiplex approach to extending optical lithography, Chen X L, Brueck S R J, Journal of Vacuum Science and Technology B, vol. 16, pp. 3392-3397 (1998), in U.S. Pat. No. 5,759,744 to Brueck et al., in U.S. Pat. No. 6,233,044 to Brueck et al., and U.S. Pat. No. 6,042,998 to Brueck et al, the entire contents and disclosures of which are hereby incorporated by reference.

For the interference of two plane waves in air, the period is given by $\lambda/(2 \sin \theta)$ where $\lambda$ is the optical wavelength and $\theta$ is the angle of incidence. For a 213-nm laser source (fifth harmonic of YAG) this gives a period of about 150 nm (for $\theta=80$ degree). It is important to realize that this limit is on the period, not on the feature or structural dimensions. Nonlinearities in the exposure/develop processes and in subsequent processing allow reduction of the features to dimensions well below $\lambda/4$.

Thus, nanochannels of about 1 to about 1000 nanometers (or 10 to 300 nanomaters) can readily be developed in a substrate. The ultimate limit in channel width is set by material properties and by uniformity of the processing; nanochannel widths as small as 5 to 10 nm are routinely achieved.

The use of immersion techniques, may further reduce the period by a factor of the refractive index, approximately a factor of 1.5, to a period of about 75 nm.

Water and higher-index liquids, including liquid Argon (n about 1.6) may be used to further extend these results into the sub-100-nm period regime that will be important for biological separations. Thus, for example, immersion interferometric lithography can be employed where the grating period has been reduced to 90 nm with exposure by 193 nm light using immersion in deionized water.

Nonlinear processes may be used to further reduce the period. Thus, for example, a photoresist line can be interpolated between two parallel lines that have already been transferred into a nitride layer. The final period is about half of the initial IL period. Extending the calculation above with this spatial period division gives a period of about 37 nm and a dense linewidth of about 17 nm ($\lambda/12$). Importantly, all of these results are macroscopic in scale, e.g., covering areas of about 1 $cm^2$ or larger. One advantage of optics is the parallel nature of the exposure, which may extend a centimeter or more. For a square lattice with a 100-nm pitch and a 1 cm field, there are $10^{10}$ features, well beyond the realistic capabilities of serial techniques such as e-beam and scanning probes. In particular embodiments of the present invention, IL may be extended deep into the nanometer regime (either to feature sizes of about 10 nm or nearest-neighbor distances (aperture sizes) of <10 nm, but not both simultaneously).

Continuously varying channel spacing between nanostructures is desired for many of the bio-separation applications such as various nanofluidic configurations discussed herein.

One approach to a graded structure is to macroscopically vary the intensity across the plane of exposure while keeping the other interference conditions, such as the angles between the light propagation vectors and the polarization, unchanged. One such variation of intensity would be a smooth gradient in intensity of one of the two interfering light waves. This results in interference fringes with uniform spacing but different intensities. The difference in intensity of the fringes leads to differences in exposure of the photoresist used. Because the fringe spacing is not changed, the pitch is uniform. The interference pattern would have even better contrast if both light waves had the same gradient in intensities.

When a positive photoresist is used, the areas corresponding to fringes with stronger intensities leave wider cavities in the photoresist after exposure and developing. The areas corresponding to fringes with weaker intensities leave narrower cavities in the photoresist. When the substrate is etched, these differing widths translate into features in the substrate that have differing widths. The features have the same pitch, however, because the fringe spacing is not altered. This leads to a constant pitch, but a varying line:space ratio. This procedure provides a continuously decreasing channel width that may be accurately controlled over very long distances. Such gradient separation matrices exhibit the favorable traits of gradient gels (high resolution in separation), without the difficulty and irreproducibility associated with their preparation Similarly, this technique when used with negative photoresist leaves wider features in the areas corresponding to fringes with weaker intensity and narrower features in the area corresponding to fringes with stronger intensity.

An alternative approach may produce features with a gradient in width and pitch. This may be easily achieved with IL by using a cylindrical lens in one of the beams, while keeping the other beam as a plane wave. In this case the plane of exposure becomes a chord for a number of circular wavefronts. Because the wavefronts have different radii of curvature (spacing of an optical wavelength), the spacing between the interference fringes, as well as the width of the interference fringes, vary along the length of the plane containing the interference fringes on the surface of the photoresist coating the substrate. Similarly, curved surfaces (sections of Newton's rings) may be formed by interfering a plane wave and a spherical wave or two spherical waves of differing radii of curvature.

Other types of separation systems may involve discontinuous gradients. One such system may have differing aperture sizes that may be produced by separate exposures with different intensities, at different pitches through shadow masks, or by using multiple exposure techniques to eliminate rows and/or columns of pillars in certain areas of a previously exposed uniform nano-structured surface.

Variations in size may also be produced chemically. For example, increasing the oxidation of silicon in certain areas of a chip will result in a swelling of the features, reducing the width of some channels while conserving the pitch of the features. Similarly, macroscopic areas may be selectively functionalized with monolayers, reducing the width of channels contained in that area.

One may also electrochemically produce silicon carbide on a silicon substrate. Silicon carbide is suitable for sublimation growth, allowing one to control the width of the modified channels in a certain area. Of course, silicon carbide is only one example of surface modifications that can be performed.

One may also selectively heat a substrate, bringing it close to its annealing temperature. At this time the substrate may be placed under a highly controlled stress. The subsequent strain alters the size of channels. A gradient in temperature across the substrate results in a gradient of strain, and therefore a gradient in channel widths. This technique would only be suitable for substrates without a crystalline structure (such as glass or amorphous silicon, for example).

The nanochannel devices may be further modified by oxidation. This provides insulation between the silicon and the surrounding material (allowing electrophoretic fluidic manipulation) and varies the surface interactions between the nanostructure and the surrounding materials for fluidic applications. Very high aspect ratio, crystal-structure-independent etching processes have been developed to address the need for 3D structures in MEMs technology. These involve pulsed gas processes in which an isotropic etch process is alternated with a surface passivation step to reduce the sidewall etch rate and only etch feature bottoms exposed by ion bombardment. To date, these processes have largely been investigated on micrometer scales, as part of the present invention they are extended to the nanostructured regime. This greatly broadens the available classes of materials for which deep, high aspect ratio structures suitable for nanofluidic applications may be fabricated.

A substrate can also be coated with photo-resist or a light-sensitive coating. A template with the patterns of chip components on it can be projected onto the substrate using light, for example, intense ultraviolet light. The parts of the chip that are exposed to the light can then be etched with gases and/or showered with ions to create transistors. Such transistors can be formed along the length of one or more nanochannels. The transistors can be connected when later cycles of the fabrication process lay down metal and insulation. Thus, the devices of the invention can include transistors (which act as electronic amplifiers, oscillators, or, most commonly, switches), in addition to other components such as resistors, diodes, capacitors, and wires.

Nanostructures that exhibit a gradient in their capacity to transport biomolecular species (through size exclusion or otherwise) may be created by the IL processes discussed herein. Such gradients make separation matrices feasible for highly efficient separation of molecular species. Molecular species may be driven in the direction of the gradient, and thus separated based on their tendency to traverse the gradient, by a variety of driving forces, including, but not limited to, electrophoresis, externally-applied pressure, capillarity, diffusion, and osmosis.

IL represents a convenient method for generating nanostructured separation matrices that contain physical gradients that allow selective transport of chemical species and, thus, may be used to achieve a separation of different chemicals. When compared to other nanolithographic methods of pattern generation (e.g., electron beam lithography, scanning probe lithography), it is more convenient, efficient and inexpensive because it may be used to generate the entire pattern in one, parallel step and is not, a serial "writing" technique. Other parallel techniques (e.g., imprint lithography) rely on a primary patterning technique to generate a master that may then be used to produce replicas of nanostructured features in a parallel fashion. While IL is a preferred method to generate nanostructured gradients for molecular separation, a variety of methods could be employed to generate the nanostructured matrix gradient "artificial gels" of the present invention. Gradients in the chemistry of the separation matrix may be prepared by a variety of methods as well, including those based on IL.

The use of IL allows such nanostructured separation matrices to be produced easily and very inexpensively. Nanostructures in which channels are on the order of the excluded size of dissolved biomolecules allow an enhanced flexibility in separation. Higher resolution may be obtained in combination with any of the following mechanisms namely, size exclusion, electrophoretic mobility, isoelectric point, asymmetric diffusion, entropic trapping, hydrophobic interaction and affinity interaction (molecular recognition), as well as others. The gradient matrices produced allow efficient separation and identification of biomolecules such as native proteins and protein complexes in addition to denatured proteins and nucleic acids.

Nanolithography-generated systems have advantages over conventional systems such as gels in terms of (1) the virtually perfect uniformity of pore size and pore size distribution from device to device, and (2) the flexibility to precisely define the required distribution (gradient) of pore sizes and pore chemistries. This high degree of reproducibility and versatility in nanofabrication will result in the ability to construct separation devices that exhibit unprecedented degrees of flexibility (resolution, dynamic range) and reproducibility in their separation characteristics.

The separation gradient may be formed by a variety of means including, for example, nanolithography (e.g., IL, electron beam, local probe, nanoimprint) and pattern transfer (etching, deposition, lift-off) means.

Nanostructured gradient (chirped) separation matrices may be formed by a variety of means including nanolithography (e.g., IL, electron beam, local probe, nanoimprint) and pattern transfer (etching, deposition, lift-off) means. FIG. 3 illustrates a graded array of nanostructures. The aperture size between the nanostructures approaches molecular dimensions.

Multiple-exposure IL moire patterns provide for cyclic gradients that may be used for simultaneous manufacture of multiple structures. Gradients may also be fabricated across uniform patterns by non-uniform deposition or etching using properly designed deposition and/or etching tools and techniques such as oblique incidence of etch/deposition atomic/molecular species (shadowing). Analogous techniques may be used in generation of gradients in surface modification chemistry incorporated into the array.

As an example of channel formation according to the present invention, IL and anisotropic wet etching of silicon allow the creation of open, parallel nanostructured channels (e.g. uncapped in the direction perpendicular to the surface) with lateral features on the order of biomolecular length scales (about 1-10 nm) but with overall dimensions reaching the microscopic (about 100 μm) or even macroscopic (about 1 cm or greater) scales. Depending upon the dimensions, molecular transport mechanisms may include diffusion, electrophoresis or bulk-flow. The relatively large vertical scale is sufficient to allow high throughput of molecules and external pumping using either electrokinetic or electro-osmotic forces. Such architectures are applicable to channel and post arrays that are of interest for the separation of proteins and large DNA molecules.

Arrays of nano structures (either of uniform size or with a gradient of sizes) may be surface-modified with chemical species that enhance the separation characteristics of the matrix. These chemical species may be distributed uniformly over the nanostructured separation matrix or may be distributed in a gradient (continuous or discrete) in the direction of separation over the matrix. These chemical species may include small organic molecules, polymers, receptors or other biomolecules.

IL may be used to expose patterns on photoresist on silicon, germanium or other materials (which are later etched). Silicon, germanium and some other materials may have an oxide surface that is easily modified with silanization reagents. Synthetic strategies for modification are also available for other materials (besides oxides), including native silicon and noble metals (e.g., gold). Monomolecular layers may be created from a wide range of commercially- or synthetically-available chemical species that will enhance separation characteristics based on the type and degree of interaction of chemical species being separated with the walls of the surface-modified nanostructured separation matrix. Examples of types of surface modifications (either as gradients or uniform) include the use of hydrophilic oligomeric and polymeric species e.g., poly-ethylene glycol (PEG) to minimize interactions of chemical species especially proteins, with nanostructured surfaces; use of hydrophobic molecular or oligomeric species to elicit hydrophobic interaction of chemical species (esp. proteins) with nanostructured surfaces; use of mixtures of hydrophobic and hydrophilic species (polar, apolar, H-bonding, ionic) to tune interaction of different chemical species with surfaces; use of ionic molecular species and mixtures of ionic species to tune interaction of different chemical species with surfaces; use of biomolecular or organic receptors to elicit molecular recognition of small molecules, polymers, proteins, DNA, RNA, or oligonucleotides with the surface; use of oligonucleotide probes to tune interactions of DNA, RNA or nucleic-acid binding proteins with the surface; use of cyclodextrins, macrocyclic antibiotics, crown ethers and other chiral selectors to tune enantiomeric interactions of chemical species with the surface; and use of stimuli-responsive (smart) molecules or polymers to allow external control of interaction of chemical species with the nanostructured surface.

Other types of separation systems of the present invention may be thought of as having discontinuous gradients. These separation systems contain areas with different aperture sizes, and may be made either by separate exposures at different intensity, at different pitches through shadow masks, or by using multiple exposure techniques to eliminate rows and/or columns of pillars. Such systems are especially useful in that they will allow recovery of separated compounds (purification). Thus, for example, a mixture of negatively charged biomolecules (e.g., SDS treated proteins or DNA) can be loaded at one end or corner of the nanochannel device and the biomolecules are driven electrophoretically across a series of discrete "sieves" that have increasing aperture size, such that smaller, and then larger molecules pass through the consecutive sieves. Each sieve is connected to a separate outlet port, such that different sized biomolecules may be collected at different outlets. If necessary, these attachments may be made through the top or bottom of the chip, and additional separation in this direction may then be combined with recovery. More sophisticated designs allow continuous purification and sample recycle.

The invention is further illustrated by the following non-limiting Examples.

Example 1

Detection of Biomolecules in Nanochannels

Fluorescence Microscopy (FS): Some methods typically used to probe fluid dynamics in macroscopic and microscopic channels may have limited application in the investigation of electrokinetically driven flows in nanochannels. For example, a tool that is typically used in measuring flow profiles in conduits, velocimetry, may not be used for far field imaging in the present devices because the characteristic width of the nanochannels, in which non-plug-like electro-osmotic flow is anticipated, is below the diffraction limit. Near field imaging techniques may be used to obtain information on velocity distributions using fluorescent tracers, but some re-engineering of the fabrication steps and chip architecture may be needed. For the solutes and solutions of interest here (aqueous solutions of dyes, biomolecules and proteins), such adaptations would be of limited utility because dispersion in the nanochannels will typically occur by diffusion rather than by convection. This conclusion is based on Taylor's analysis and can be understood by the magnitude of the Peclet number (Pe=vh/D); where v is the average fluid velocity in the channel, h is the channel width, and D is the diffusivity of the solute of interest. H. S. Fogler, in Elements of Chemical Reaction Engineering at p. 877-880, $3^{rd}$ ed. (Prentice Hall, Upper Saddle River, N.J., 1999).

Figure 7:
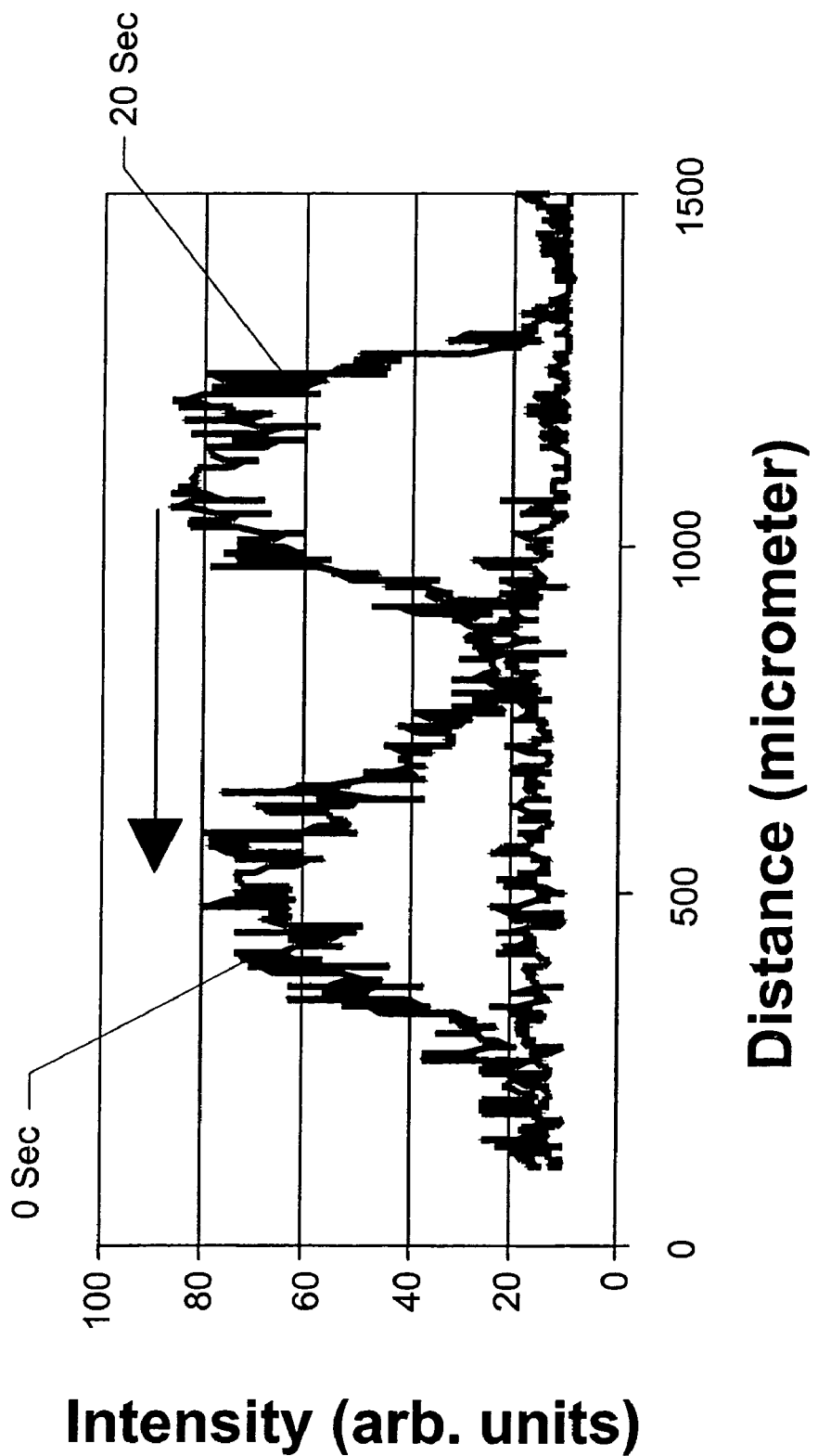
FIG. 7 illustrates the electrokinetic motion of a "band" of fluorescent dye (Alexa 532) through a nanochannel array. The band was formed using the electrical manipulation of flow in the "T-chip" shown in FIG. 1.

In preliminary experiments, solutions of fluorescent dyes were used to measure electrokinetic transport in the nanofluidic T-chip devices described herein (see FIG. 1). These chips were designed to enable the formation of sample plugs within the nanochannel array. FIG. 7 provides an example of the dispersion that occurs as the fluorescent band is transported down the channels electrokinetically. In this case a negatively charged dye was examined, however, neutral dyes could be employed to completely isolate electro-osmotic effects. Such experiments were useful for determining v, the average velocity of dyes within the nanochannels (in this case about $3\times10^{-3}$ cm/s). The dispersion of the plug was clearly evident as the flow proceeded down the channel. The Peclet number in this experiment (h=100 nm, D=$10^{-5}$-$10^{-6}$ cm$^2$/s) was small (Pe about $10^{-2}$). These results indicate that the axial dispersion observed as the fluorescent band flowed through the nanochannels was due to diffusion of the dye. Thus, fluorescent dyes may be useful in evaluating the average electrokinetic velocities of molecules in the present nanochannel devices. However, fluorescent dyes may not be as useful in flow situations in which dispersion due to convection (Taylor dispersion) is used to infer electro-osmotic velocity profiles within individual nanochannels.

Electrochemical Impedance Spectroscopy (EIS): Direct interrogation of the structure of the electrical double layer and its effect on ion transport is possible through electrochemical impedance spectroscopy (EIS). See, e.g., Chazalviel et al. J. Electroanal. Chem. 509: 108-118 (2001). Because silicon is a good conductor relative to the electrolyte solutions of interest, it is possible to use the silicon chip as a working electrode during such experiments. Moreover, the oxide thickness can be varied to isolate the capacitance of the double layer and examine how it affects ionic transport within the nanochannels under varying electrolyte conditions.

In preliminary experiments, EIS was used to determine the ionic conductivity of electrolytes in nanochannels. The experimental setup included a cell with two reservoirs and two high surface area, mesh platinum electrodes. A standard electrolyte with a resistivity of 4.5 MΩ/cm was used. Due to the high resistance of nanochannels and the high surface area of platinum electrodes, a two-electrode configuration was used for the initial EIS measurements. The DC offset was set to zero, and the applied AC frequency ranged between 0.1 Hz and 50 KHz. The collected impedance spectra were represented in the Bode diagrams (the magnitude and phase of impedance as a function of frequency) shown in FIG. 8A-C. The EIS data collected with a nanochannel device that did not contain channels demonstrated a capacitive behavior (the phase shift of −90 degrees) over the whole frequency range. In contrast, the EIS data collected with a device that had nanochannels showed a resistive component connected in parallel to the capacitance (the phase increased to −30 degrees at low frequencies). This observation was attributed to the presence of ionic conductance through the channels.

In these preliminary measurements, the measured ionic resistance of the nanochannels was about 30 MΩ, about 2 orders of magnitude below the measurement limit of our EIS system. To obtain a greater dynamic range for these measurements, the experimental setup can be optimized by increasing the total cross-sectional area of the nanochannel array (i.e., denser array, wider chip, and deeper nanochannels) and by decreasing the length of the nanochannels.

Time-resolved Fourier Transform Infrared Spectroscopy: Fourier transform infrared (FTIR) spectroscopy has been widely used to investigate the double layer structure; surface adsorbates and their orientation; and the pH at the electrolyte-substrate interface. Chazalviel et al., Appl. Spectrosc. 47:

1411-16 (1993); Sukhishvili & Granick, J. Phys. Chem. B 103: 472-79 (1999); Marinkovic et al., Electrochim. Acta 41: 641-51 (1996); Probst & Thull, Ber. Bunsenges. Phys. Chem. 99: 158-163 (1995); Harrick, Internal Reflection Spectroscopy (Wiley, New York, 1967). This technique is extended further here by interlacing the nanofluidic channels with either a Si or Ge multiple internal reflection (MIR) crystal. The reason for choosing Ge in addition to Si is that Ge waveguides provide a much wider observable range of wave numbers. A typical 50-mm-long, 2-mm-thick Ge waveguide is transparent to mid-IR (2.5 µm to 15 µm) whereas a similar Si waveguide is opaque at wavelengths longer than 7 µm. The principles behind MIR-FTIR spectroscopy are discussed in numerous publications including, for example, Mirabella, Francis, Infrared Reflection Spectroscopy, vol. 15 (Marcel Dekker, Inc., New York, 1993); and Barry & Matthews, Biochemistry 36: 15632-42 (1997). The infrared technique complements other optical diagnostics while eliminating the need for fluorescence labeling.

Figure 9:
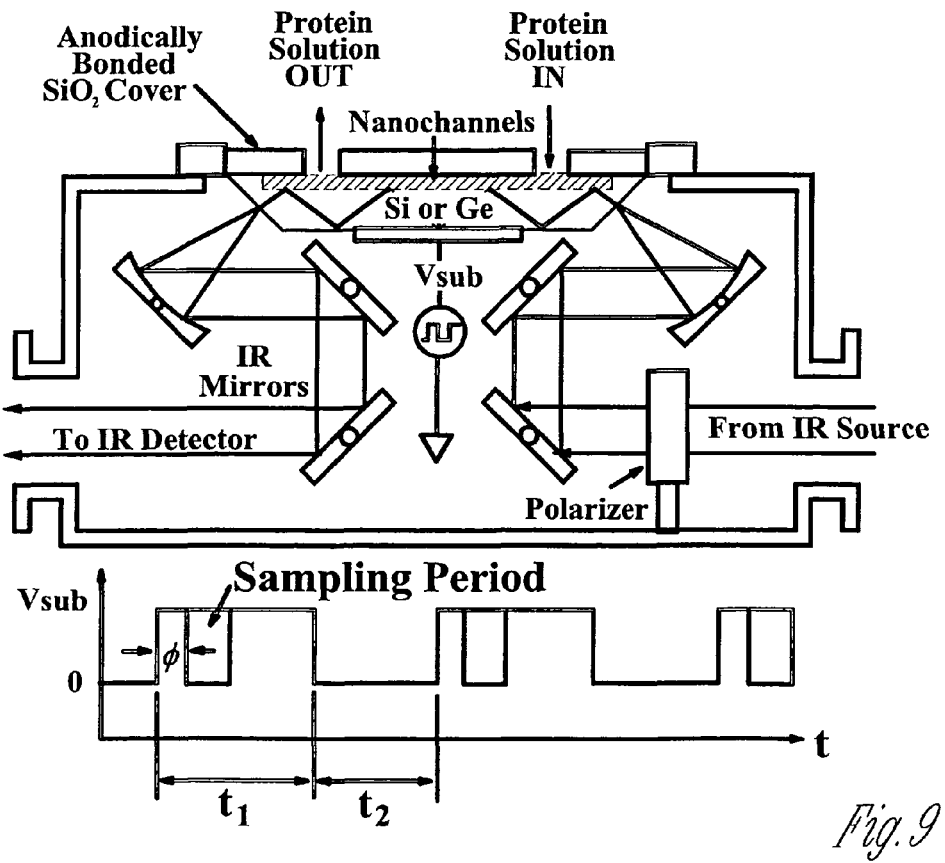
FIG. 9 is a block schematic diagram of an experimental setup that can be used to probe the double layer by modulating the potential applied to the chip substrate and monitoring the changes in infrared (IR) absorbance at 500 nsec resolution.

FIG. 9 schematically illustrates the experimental setup that can be used to investigate the double layer. The nanochannels are sealed with a Pyrex cover by anodic bonding. The protein solution enters one end of the nanochannels and exits on the opposite end. Note that in systems employed in preliminary experiment, a thin layer (~100 nm) of thermal $SiO_2$ insulated the Si and Ge substrates from the electrolytes in the protein solution, minimizing the Faradaic reactions. Similar to electrochemical impedance spectroscopy, the substrate potential is modulated, and the IR absorbance is monitored as a function of time.

The changes in IR absorbance may come from the concentration changes of IR-active species (e.g., $[H_2PO_4]^{2-}$, $[SO_4]^{2-}$, $H_2O$, and protein molecules) within the double layer. Sukhishvili & Granick, J. Phys. Chem. B 103: 472-79 (1999); Probst & Thull, Ber. Bunsenges. Phys. Chem. 99: 158-163 (1995); Harrick, Internal Reflection Spectroscopy (Wiley, New York, 1967). The changes in IR absorbance may also come from the alignment of surface adsorbates in response to the applied potential (e.g., SiOH, Si—H, C—H, $H_2O$, and protein molecules). Marinkovic et al., Electrochim. Acta 41: 641-51 (1996); Harrick, Internal Reflection Spectroscopy (Wiley, New York, 1967). In addition, the pH changes that influence the apparent absorbance from O—H stretching mode of $H_2O$ near the interface can cause changes in IR absorbance. Harrick, Internal Reflection Spectroscopy (Wiley, New York, 1967). One way of differentiating these changes is to modulate the magnitude and frequency of the potential applied to the substrate. For example, a square-wave potential can be applied that varies from 0 to +10~100 V. The changes in IR absorbance can be monitored with a time-resolution that can be as fine as 500 nsec for a 40-µsec window.

A "step-scan" approach may also be used where the mirror in a Michelson interferometer moves incrementally (400 points per excursion). The step-scan eliminates coupling between the sample modulation frequency and the scanning frequency of the Michelson interferometer in continuous scan mode, thus enhancing the signal-to-noise ratio. While the mirror is stationary at one incremental position, the potential applied to the Si or Ge substrate ($V_{sub}$) modulates, and the IR absorbance is detected in synchronization with the up-swing in $V_{sub}$. A varying phase lag ($\phi$) is introduced to decouple the electrolyte response from that of protein molecules. That is, the changes in IR absorbance due to the electrolytes would register with a smaller phase lag than the proteins since the electrolyte mobility is higher than that of protein molecules. Chazalviel et al., Appl. Spectrosc. 47: 1411-16 (1993); Sukhishvili & Granick, J. Phys. Chem. B 103: 472-79 (1999). The time-resolved measurements will delineate the changes in IR absorbance due to electrolytes, proteins, and their surface adsorbates. In particular, the characteristic time constant of electrolytes, when properly used with an equivalent circuit model, translates to the electrolyte concentration and its impedance. This indirect measurement of electrolyte impedance will be compared to the results from electrochemical impedance spectroscopy.

Example 2

Probing Protein Structure and Orientation in Nanochannels

This prophetic Example focuses on how the unique characteristics of nanochannels influence the structure and orientation of protein molecules as well as their biofunctional activities. That is, how to measure the effects on proteins of nanochannel geometry, double layer overlap, pH modulation, "gate" potential for the field effect transistor (FET) analogue, and externally applied electric field for electrophoresis. In response to these perturbations, experiments may be performed to determine whether:

the protein molecules assume a preferred orientation,
the protein molecules remain native or unfold (denature),
the protein molecules reversibly or irreversibly adsorb on the channel walls,
the protein molecules indiscriminately or selectively adsorb on the functionalized channel walls, and
the biomolecular complexes bind or dissociate in response to a "gate" voltage.

The investigation will also answer how these interactions affect protein transport and, ultimately, separation. Our scientific goal is to understand the changes imposed on the biomolecules in the nanochannels with respect to their transport properties.

Figure 12:
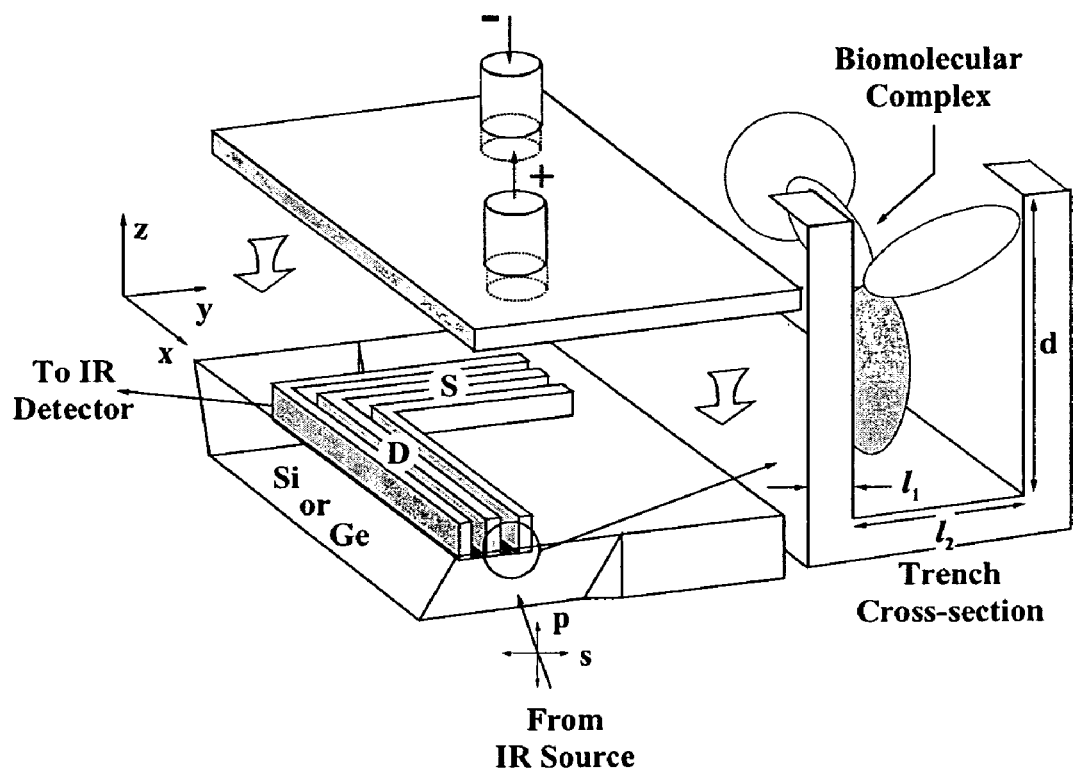
FIG. 12 is a block perspective of the architecture of Nanomachined-Waveguide-Assisted Fourier Transform Infrared Spectroscopy (NWA-FTIRS) to probe protein structure and orientation. Section S is a region where biomolecules are separated based on their electrophoretic mobility, and Section D is a region where the biomolecules are detected and analyzed. The incident IR beam can be either s-polarized to produce $E_y$, or p-polarized to produce $E_x$ and $E_z$ evanescent fields.

Nanomachined-Waveguide-Assisted Fourier Transform Infrared Spectroscopy (NWA-FTIRS): Nanomachined-waveguide-assisted Fourier transform infrared spectroscopy (NWA-FTIRS) can be employed to perform these experiments. FIG. 12 schematically shows the substrate architecture that can be used to conduct NWA-FTIRS. FIG. 12 is essentially a magnified view of the substrate shown in FIG. 9. The IR beam from a spectrometer enters a 45°-beveled edge of a Si or Ge crystal, undergoes multiple internal reflections, and exits the opposite beveled edge. With un-polarized IR, the internal reflection creates an evanescent electromagnetic field with all three components ($E_x$, $E_y$, and $E_z$) at the substrate-electrolyte interface. The multiple internal reflections essentially enhance the IR absorption by the characteristic vibrational modes of electrolytes, proteins, and their surface adsorbates.

The absolute dimension of the nanochannel width ($l_2$) is much less than $\lambda/2$, where $\lambda$ is the wavelength of the mid-range IR (2.5 to 15 µm). Previous investigation by the inventors has shown that the nanoscale surface corrugation virtually eliminates the scattering of IR upon internal refection from the top surface. In FIG. 12, Area S consists of rows of channels in which the biomolecules with different electrophoretic mobility advance to varying lengths. The separated molecules will be sequentially detected and analyzed in Area D. Although a proper choice of channel length for Area S may lead to sufficient separation of proteins, one may detect IR absorbance from multiple species of proteins as they advance in Area D. For deconvolution of the resulting absorbance signal, one can utilize chemometric/multivariate techniques (Rahmelow et al., Anal. Biochem. 257: 1-11 (1998); Heise et al., Appl. Spectrosc. 48: 85-95 (1994)), and estimate the composition of protein mixtures. To facilitate the identification procedure, one can additionally utilize difference and $2^{nd}$ derivative spectra. Zscherp & Barth, Biochemistry 40: 1875-83 (2001); Weert et al., Anal. Biochem. 297: 160-69 (2001); Jakobsen & Wasacz, ACS Symp. S. 343: 339-61 (1987). To date, the inventors have successfully integrated the nanochannels into Si MIR crystals to strictly analyze a prescribed protein solution at a time.

One can use the dichroic ratio of s- and p-polarized infrared (IR) absorbance to probe the structure and orientation of protein molecules entrapped in nanofluidic channels. See, Jakobsen & Wasacz, Appl. Spectrosc. 44: 1478-90 (1990); Kirsch & Koenig, Appl. Spectrosc. 43: 445-51 (1989); Marrero & Rothschild, Biophys. J. 52: 629-35 (1987); Marrero & Rothschild, FEBS Lett. 223: 289-93 (1987); Singh et al., J. Protin Chem. 9: 705-13 (1990); Wasacz et al., Biochemistry 26: 1464-70 (1987); Vigano et al., Biopolymers 55: 373-80 (2000); Grimard et al., Biochemistry 40: 11876-86 (2001); Han & Aydil, J. Appl. Phys. 83: 2172-78 (1997). By linearly polarizing the incoming IR beam (see FIG. 12), one can selectively excite vibrational modes whose dipole orientations are aligned with x- and z-axes (p-polarization) or with y-axis (s-polarization). The polarization technique yields the dichroic ratio (D) defined as:

$$D \equiv A_p/A_s = (E_x^2 + 2E_z^2 \cot^2\theta)/E_y^2 \quad (6)$$

where $A_p$, $A_s$, and $\theta$ represent the p-polarized IR absorbance, the s-polarized IR absorbance, and the dipole moment orientation with respect to z-axis. Note that $E_x$, $E_y$, and $E_z$ are functions of refractive index of the protein solution whose extinction coefficient is directly proportional to the IR absorbance. One can calculate $E_x$, $E_y$, and $E_z$ for the given geometry, substrate, and solution in a self-consistent manner, using the Kramers-Kronig dispersion relation. Silverstein et al., Spectrometric Identification of Organic Compounds, $4^{th}$ ed. (John Wiley & Sons, New York, 1981). For the nanochannel devices of the invention, D>2 indicates that the subject dipole moment is preferentially aligned parallel to x- and z-axes, whereas D<2 indicates that the subject dipole moment is preferentially aligned parallel to the y-axis. Marinkovic et al., Electrochim. Acta 41: 641-651 (1996). To apply this analysis to protein molecules, one can focus on α-helices and β-sheets that largely comprise protein molecules. For α-helix structure, the transition dipole moment is parallel to the helix axis for the Amide I band near 1655 cm$^{-1}$ (C=O stretching mode) and perpendicular for the Amide II band near 1547 cm$^{-1}$ (H—N—H bending mode). The opposite is true for β-sheet structure. Thus, the dichroic ratio carries information on the secondary structure of proteins and helps differentiate the orientation of proteins in the nanochannels. As contemplated herein, the proteins would assume a preferential orientation, in response to the physical restrictions of the nanochannels, the double layer overlap, the electrophoretic potential, the modulated substrate bias, the pH changes, and the channel internal surfaces passivated with functionalized self-assembled monolayers (SAMs).

Figure 13:
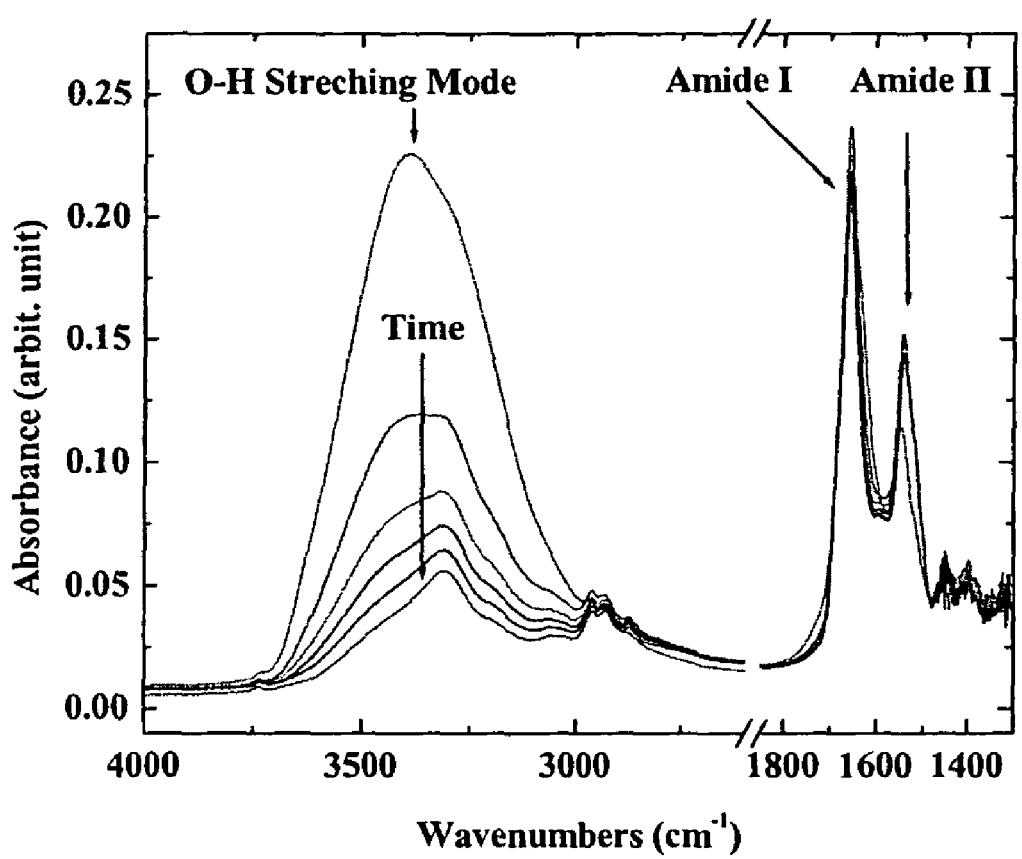
FIG. 13 is a graph of a series of infrared (IR) absorbance spectra of bovine serum albumin (BSA) in nanochannels as detected by MWA-FTIRS. The initial concentration of BSA was 1 mg/mL in phosphate buffered saline. The spectra were taken over time as $H_2O$ evaporated from the solution.
Figure 14:
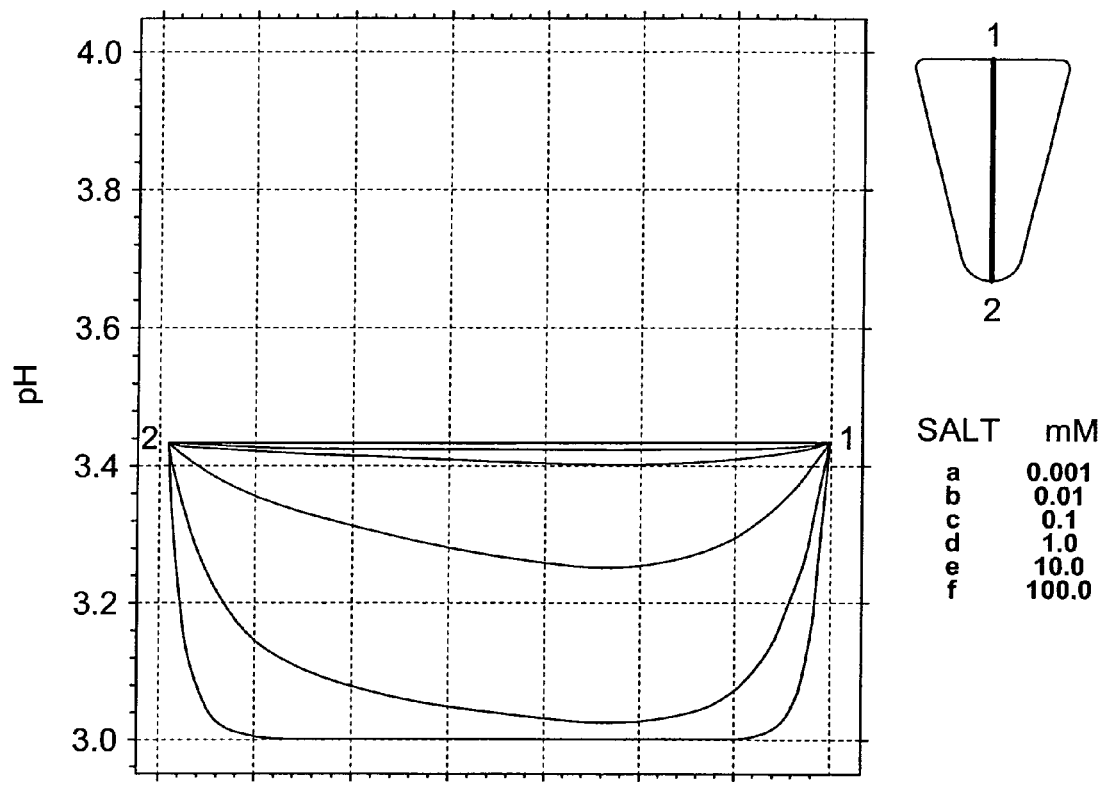
FIG. 14 provides an estimated pH distribution along the centerline (bottom 2 to top 1) of a 60 nm channel as a function of unbuffered salt concentration. To correlate these simulations with experimental measurements, the concentration distribution of the dye will also have to be included in the pH averaging algorithm.

FIG. 13 shows IR absorbance of bovine serum albumin (BSA) solution injected via capillary action into 100-nm-wide, 200-nm-deep nanochannels fabricated at a 300-nm pitch. In these dimensions, the biomolecules exist well within the typical depth of penetration for the evanescent field. The concentration of BSA is 1 mg/mL in phosphate buffered saline. The O—H stretching vibrational mode of H$_2$O near 3400 cm$^{-1}$ decreases during H$_2$O evaporation while the Amide I and II regions remain more or less constant. This result indicates that the bending mode of H$_2$O near 1596 cm$^{-1}$ is unusually suppressed in the nanochannels. A comparison of a flat MIR crystal and a nanomachined MIR crystal confirmed this observation. The minimal interference from H$_2$O fortuitously improved the reliability of using Amide I and II peaks for the purpose of determining protein structure and orientation. Because the absolute number of BSA molecules remains the same in the channels, and the entire volume was probed inside the nanochannels, the intensity of Amide I and II absorbance peaks remains nearly constant. This preliminary experiment demonstrates that (1) protein molecules can be injected into nanochannels by capillary force and (2) Amide I and II peaks can be reliably used to determine protein structure and orientation.

To systematically build the relationship between IR absorbance and protein structure/orientation, the following can be probed. Water soluble proteins that consist almost entirely of α-helices (e.g., BSA, myosin, collagen, and parvalbumin) or β-sheets (e.g., Fab fragments) can be analyzed to ascertain how α-helical proteins and β-sheet proteins respond in the nanochannel environment. For instance, BSA in its native state consists mostly of α-helices and little to no β-sheets. These proteins provide a convenient way to determine their orientation in the nanochannels. Proteins that contain a heme group bonded to CO (e.g., horse radish peroxidase (HRP)-monoclonal anti-HRP complex, hemoglobin, and myoglobin) have signature IR peaks associated with CO bound to heme in HRP located near 1934 and 1905 cm$^{-1}$. These peaks are very distinct from amide absorbance peaks of common proteins that appear in the 1600-1700 (amide I), 1500-1600 (amide II), and 1200-1350 cm$^{-1}$ (amide III) regions.

Example 3

Electrokinetic Measurements in Nanochannels

Fluorescent Dye Probes: Commercially available pH-sensitive, fluorescent dyes such as fluorescein and its derivatives, e.g., SNARFs or BCECFs from Molecular Probes, can be used as probes to measure the extent of the pH shift in nanochannels. The experiments themselves are relatively straightforward: a dye is selected which has the same charge sign as the channel wall (to minimize interference from surface adsorption) and a buffer is selected with a pH in or near the middle of the dye's peak transition range. The dye is then excited at an appropriate wavelength, its emission spectrum recorded and the pH is determined as a ratio of emission spectra peak wavelengths or as a peak shift. In the nanochannel, the pH shift as a function of ionic strength will be tested by varying the amount of neutral salt, NaCl, in the buffer. The associated control experiment is a pH measurement at high salt, e.g., >100 mM NaCl. This same approach can be used for the FET analogue experiments with the caveat that the current into the gate electrode at steady-state will have to be monitored in the sub-picoamp range to make sure that current leakage into the nanochannels, and the concomitant electrolysis reactions, are not responsible for the pH shift in the channel.

ζ-Potential Dye Probes: Neutral fluorescent dyes can also be used to determine ζ-potentials either by peak or frontal analysis, depending on how the dye sample is applied to the channel. In frontal analysis the leading edge of the sample can be monitored using a confocal microscope and the ζ-potential extracted from the observed velocity using extensions of D-H theory to small channels.

Impedance Spectroscopy: Electrochemical Impedance Spectroscopy (EIS) can be employed to investigate the effects of double layer modulation on the ionic transport in nanochannels. In order to achieve this objective, an understating of the metal/silicon/silica/electrolyte interface is necessary. EIS experiments are expected to allow for separation of the capacitance due to the double layer from capacitances associated with other interfaces. Determination of the double layer capacitance is important in order to establish to what degree it is possible to change the DC voltage across the double layer by applying an external DC voltage between the metal/silicon/silica/electrolyte interface and a reference electrode. Changes in the DC potential profile across the double layer with the external bias are expected to translate into changes in the ionic conductivity through nanochannels. An alternative approach to investigate the effects of the double layer on the ionic conductivity through nanochannels would be to directly measure ionic conductivity as a function of the external DC voltage between the metal/silicon/silica/electrolyte interface and a reference electrode.

Figure 15:
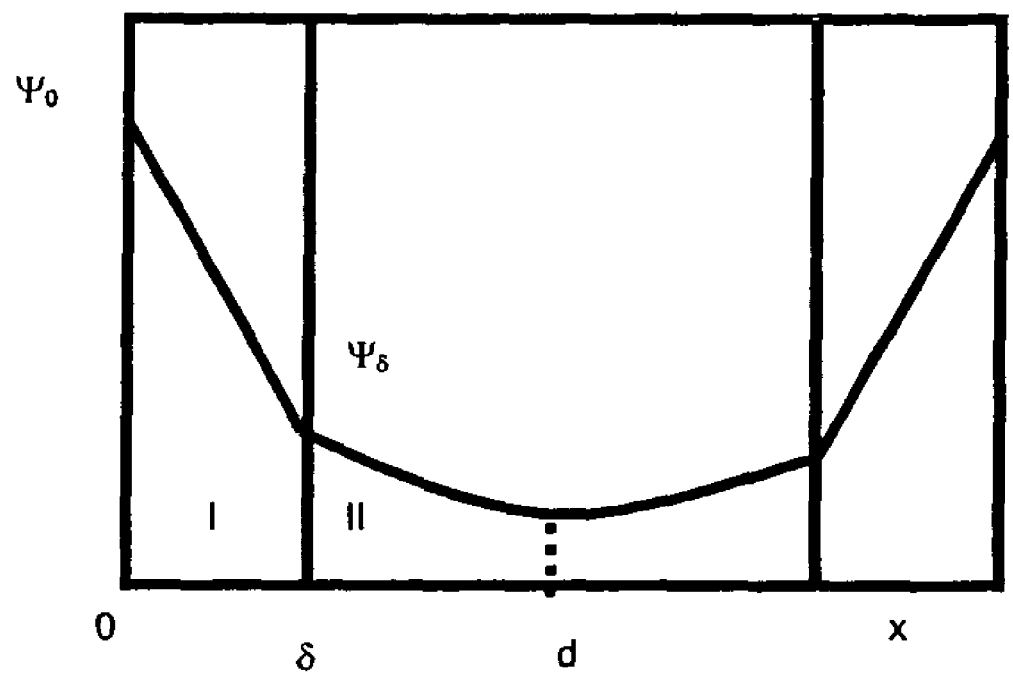
FIG. 15 illustrates the potential distribution across a nanochannel. Region I is the $SiO_2$ of the channel wall and Region II is the channel filled with salt solution. δ is the thickness of the $SiO_2$ layer and d is the half thickness of the nanochannel.

A brief theoretical analysis is suggested here that estimates the effect of the bias potential on the double layer in the nanochannel and the conductivity of the electrolyte solution in it. First, consider a nanochannel with parallel walls and infinite depth and length. The structure of the channel is depicted on FIG. 15. To preserve clarity and simplicity we assume that the potential at the $SiO_2$/solution interface is low and there is no Stern layer developed. Solving the more general case of arbitrary potential and also the presence of a Stern layer is straightforward and will be done in the future. Region I corresponds to the $SiO_2$ layer and is a non-conducting dielectric. Region II is the nanochannel filled with electrolyte solution. The question we try to answer is how the ionic distribution in the channel will change if we change the potential $\Psi_0$ at the Si—$SiO_2$ interface by applying a voltage there. To do that, we solve the equations for the potential distribution in both regions. In Region I there are no free charges, therefore the potential distribution is given by Laplace equation, which, for $\Psi(0)=\Psi_0$, $\Psi(\delta)=\Psi_\delta$ gives:

$$\Psi(x) = \frac{(\Psi_\delta - \Psi_0)}{\delta}x + \Psi_0 \qquad (7)$$

i.e., in the dielectric Region I the potential changes linearly. Note that the value of $\Psi_\delta$ is not known. In Region II the potential distribution is given by Poisson-Boltzmann equation which for $\Psi(\delta)=\Psi_\delta$, $\Psi(d)=\Psi_d$, $d\Psi/dx=0$ for $x=d$ yields:

$$\tilde\Psi(x) = \frac{4}{z}\text{arctanh}\left[\tanh\left(\frac{z\Psi_\delta}{4}\right)\exp(-\kappa x)\right] + \qquad (8)$$
$$\frac{4}{z}\text{arctanh}\left[\tanh\left(\frac{z\Psi_\delta}{4}\right)\exp[-\kappa(d-x)]\right]$$

and $$\tilde\Psi_d = \frac{4}{z}$$

arctanh $$\left[\exp\left(-\frac{\kappa h}{2}\right)\tanh\left(\frac{z\Psi_\delta}{4}\right)\right].$$

. Now an expression can be derived for the potential at the $SiO_2$/electrolyte solution interface, $\Psi_\delta$. To do that the following conditions are imposed:

$$\Psi_I = \Psi_{II}, \quad \varepsilon_I \frac{d\Psi_I}{dx} = \varepsilon_{II}\frac{d\Psi_{II}}{dx} \qquad (9)$$

at the interface with $\delta_1$ and $\in_1$ being the dielectric permittivities in Regions I and II respectively. Then:

$$\Psi_\delta = \Psi_0 - \frac{\sigma_0(\Psi_\delta)}{C_{wall}} \qquad (10)$$

where $C_{wall}=\in_{oxide}\in_0/\delta$ is the capacity of the dielectric region I. For simplicity it is assumed hereafter that $\Psi_\delta=\zeta$. This equation tells us how the potential at the $SiO_2$/electrolyte solution will change by changing the bias voltage, $\Psi_0$, the electrolyte concentration, $\kappa$, the width of the channel, d, and the thickness of the $SiO_2$ layer, $\delta$. Note that in the absence of applied bias, potential $\Psi_\delta$ will still be present and equal to the native potential of the $SiO_2$/electrolyte solution interface. $\Psi_0$ then will be induced by the drop of this native surface potential across the $SiO_2$ layer (see FIG. 15). The distribution of the electric potential in the nanochannels is given by Equations (7)-(8). Equation (8) could be used to determine how the distribution of the charge carriers (or charge density, $\rho_e$) in the solution will change with the applied bias potential. The average charge density for a binary electrolyte in a channel with overlapping double layers will be:

$$\rho_e(x) = e\sum_i z_i n_i^0 \exp\left[-\frac{z_i e\Psi(x)}{kT}\right] \qquad (11)$$

where $\Psi$ is given by (8) and $n_i$ and $z_i$ denote the number concentration of charged species and the charge number, respectively.

The average conductivity of the channel is defined by where $$K_{tot} = \frac{1}{d}\int_0^d \left\{K_{mig}(x) - \rho_e(x)\frac{\varepsilon\varepsilon_0[\zeta-\Psi(x)]}{\eta}\right\}dx, \qquad (12)$$

$$K_{mig}(x) = \frac{e^2}{kT}\sum_i z_i^2 D_i n_i^0 \exp\left[-\frac{z_i e\Psi(x)}{kT}\right] \qquad (13)$$

is the migration contribution to the total conductivity. The integral in (12) is taken over the channel cross-section. The second term in the right hand side of (12) is the current due to convective electroosmotic transport.

The conductivity depends on the wall and the bias potential through $\Psi(x)$, see Eq. (10). Note, however, that $\Psi_0$ is due not only to the applied bias voltage, but also to the potential that the $SiO_2$/electrolyte solution interface acquires upon contact (see above). This means that even in the absence of applied bias voltage, the Si/$SiO_2$ interface (x=0 in FIG. 15) will have a potential different from zero. Therefore the model provided here is applicable also to channels with overlapping double layers and in the absence of an applied bias potential. In summary, the effect of the nanochannels on the conductivity will increase with increasing potential $\Psi_0$, with increasing differences between the mobilities of the different components and will be more substantial for asymmetric electrolytes.

Example 4

Electrophoresis and Electrochromatography in Nanochannels

Because of its channel dimensions and geometries, materials properties (e.g., electrical and thermal conductivities, and the malleable surface chemistries of the $SiO_2$ layer), the nanochannel devices of the invention offer some intriguing possibilities for electrokinetic separations. It should be understood that, because the effective diameter of the nanochannels is so small, nanochannels are used in an open-channel format, i.e., unpacked with a matrix material. However, due to their large surface area to volume ration, high-performance chromatography can be carried out in the nanochannels having walls derivatized with molecular ligands, tenticular arms or shallow, sorbed phases that are anchored in the channels.

Thus, it is possible for classical HPLC to be applied to nanochannels adapted for connection to either external or integrated high pressure pumps (e.g., EK pumps) when the nanochannel lengths are long enough (e.g. in excess of 2 cm) to produce both reasonable capacities and acceptable resolutions. Solid phase extraction (SPE) is a possibility, especially as a recovery/concentration step in the sample load cycle.

Electrophoresis, on the other hand, may be better-suited to use with nanochannel devices because (1) the electric field can drive an electroosmotic flow superimposed on the separation and (2) resolution is fundamentally independent of channel length, at least to a first approximation, and is directly dependent on the applied voltage and the physicochemical properties of the channel and the molecules to be separated, e.g., the channel $\zeta$-potential and the proteins' electrophoretic mobilities. For instance, classical theory for isoelectric focusing (IEF) predicts that, if the channel length is halved but the voltage drop across the channel is held constant, then the shorter channel will have roughly the same resolution as the longer channel. Hutterer & Jorgenson, Anal. Chem. 71: 1293-97 (1999); J. W. Jorgenson, ACS Symp. S. 335: 182-198 (1987). For zone electrophoresis, a similar result is found for the number of theoretical plates, N, that it is fundamentally independent of channel length. J. W. Jorgenson, ACS Symp. S. 335: 182-198 (1987); Lee et al., Anal. Chem. 63: 464-467 (1991).

Isoelectric focusing has the additional advantage that it can be localized to a channel of virtually any (short) length by forming the focusing pH gradient between two reservoirs whose pHs bound the pIs of the target molecules. To some extent, this can also be done with isotachophoresis (ITP) by using electroosmosis to generate a counterflow to the ITP stack velocity. It turns out that, if this counterflow falls in the window between the electrophoretic velocities of the leading and terminating electrolytes, then the ITP stack will stop within this window at a prescribed, i.e., predictable, point in the channel and remain there (unpublished simulations). While the stack is sitting in this window, additional solute(s) can be added to or even removed from the stack.

The FET-analogue can also be used with the nanochannel devices of the invention to shift the surface potential and hence, the $\zeta$-potential, so that the $\zeta$-potential can be set to hold the stack in place during loading and then shift the $\zeta$-potential to mobilize the stack once the ITP zones have fully formed. Three-way tee-junctions (FIG. 16A) and four-way crosses can then be used to break out pure solute zones from the ITP "trains" for further processing, e.g., by mass spectroscopy. Note that typical concentrations in focused IEF bands are on the order of 5-10 mgs/mL or higher while, for ITP, zone concentrations are typically fall in the range of 10-50 mgs/mL or higher.

Since the various modes of electrophoresis, e.g., isoelectric focusing, isotachophoresis, and zone electrophoresis, mentioned above are limited in number and they all separate ions using approximately the same fundamental mechanisms, a set of "orthogonal" separation protocols must be adapted to the nanochannel scale and this is most readily done using the affinity, hydrophobic or ion exchange chemistries familiar to chromatography.

While chromatographic stationary phases may be formed in situ from monoliths or self-assembling emulsions, a much simpler strategy for creating a stationary phase[92] is to derivatize the surfaces of the channel with long-chain, e.g., $C_{10}$-$C_{18}$, functionalized hydrocarbons. Bach et al., Electrophoresis 22: 3902-07 (2001). Such derivatization provides significant advantages in capacity, resolution, and throughput for nanochannels over microchannels due, in large part, to their larger surface area to volume ratio. When coupled to electrokinetics in the form of electrochromatography, the same advantages available for open channel electrophoresis, e.g., high resolution in short channels, can be adapted to these columns. Furthermore, because they provide an orthogonal arsenal of separation techniques, they will allow true multidimensional processing on this platform.

It is also likely that the pH modulation engendered in the FET-analogue could be applied in nanoelectrochromatography, allowing target proteins to be bound and released by changing the voltage on the nanochannel walls (Si or Ge). For example, in protein A affinity purification of monoclonal antibodies, the bind and release steps are usually modulated by pH because the protein A will generally bind monoclonal antibodies above pH 4 and release them around pH 3. Because this modulation in the nanochannel can be carried out in the electrical double layer, it may be possible to bind and then release monoclonal antibodies by changing the "gate" potential to shift the pH. One big advantage of this approach is that an elution buffer should not be needed.

A number of different experiments will be performed to test the viability and performance of the nanochannel device as a medium for both classic and novel electrophoresis/electrochromatography separations.

Classic Electrophoresis:

The various electrochromatography and FET analogue nanochannel device configurations, can be tested and compared with existing separation platforms. This is most readily done by adapting the classic electrophoresis protocols to a nanochannel device and correlating the results in terms of plate efficiencies and resolution. Experiments that can be performed to illustrate the performance of the devices of the invention are as follows.

Isoelectric focusing (IEF): Idoelectric focusing is a good place to start because the protocols developed for capillary and microchip IEF can be applied, with little or no modification, directly to the nanochannel device. Using the hybrid nanochannel device described in FIG. 1, the device is first filled with Nanopure™ water under 70-100 psi pressure using a syringe or HPLC pump. The device is then conditioned using 100 mM KOH. This is followed by a mild phosphoric acid wash and a pure water rinse. The wells or channels leading to nanochannels are filled with protein solution in 1-4% ampholyte plus up to 0.4% methylcellulose to counteract electroosmosis. After filling the channels, the electrode reservoirs are flushed with acidic anolyte and alkaline catholyte at the anode and cathode, respectively. The electrodes are inserted into the reservoirs, and then power is applied to the electrodes. In the initial experiments, naturally fluorescent proteins, e.g., phycoerythrin, allo-phycocyanin and various forms of green fluorescent protein, will be used to track progress as the proteins focus into bands. Later experiments can be performed using fluorescent dye-labeled proteins. Detection will be carried out using either a confocal microscope or a bright field fluorescence microscope, e.g., Leica DMLB.

Isotachophoresis (ITP): In this case, following the conditioning and wash steps, the channel and reservoirs are filled with leading electrode, e.g., Tris-HCl at pH 10, and then a protein mixture dissolved in leading buffer is flushed into one reservoir. Voltage is turned on, and the protein mixture is allowed to electromigrate into the channel in moving boundary electrophoresis (MBE) mode until sufficient sample is applied to the channel. The separation is then switched over to ITP mode by flushing the upstream buffer reservoir with terminating electrolyte, e.g., Tris-EACA ($\in$-amino caproic acid), before reapplying the current until a contiguous train of "stacked" bands forms. In this case fluorescent dyes can be used in addition to proteins and detection is the same as above.

Zone Electrophoresis (ZE): Zone electrophoresis is the most difficult of the three classic electrophoresis modes attempted here because the protein bands are not self-sharpening. Instead a stacking technique will be used to sharpen the bands at the start of the run and this will be followed by isocratic or zone electrophoresis. In this case, the bands spread by diffusion as they electromigrate through the channel. Again fluorescent proteins will be used and detection is the same as in IEF.

Gradient-Channel Electrophoresis: Gradient nanochannels can be fabricated (see FIG. 3), which can then be used in electrophoretic separations. SDS-PAGE is routinely carried out in gradient gels whose pore size is gradually reduced as one moves away from the sample well, and this has the effect of increasing the range of molecular weights, which can be fractionated on that gel. Because the surface and particle double layers of the nanochannel devices are roughly the same order of magnitude as the channels, as the channel dimension decreases and double-layer overlap becomes more pronounced, it will have an effect on the proteins' effective mobility, e.g., preferentially slowing the electromigration of the larger particles, which may increase resolution according to molecular weight for protein isoforms. Proteins may also spontaneously focus in these channels due to gradient-induced pH variations, confined-particle electromobility variations and channel-surface electroosmotic flows. The protocols for gradient-channel electrophoresis will initially be similar to those used in zone electrophoresis above.

FET-Modulated Electrophoresis and Electrochromatography:

The FET-analogue described earlier can be used in a number of different ways to modulate various forms of electrophoresis and electrochromatography by using a "gate" voltage to shift the potential at the inner surface of the nanochannel. Several possibilities are as follows.

FET-Isotachophoresis: In classical ITP described above, the stack will eventually migrate off the end of the channel, into the leading electrolyte well where it will be lost, and it may do so before the stack is fully formed. Using the FET analogue, a "gate" voltage can be used to shift the $\zeta$-potential so that the electroosmotic velocity falls between the electrophoretic velocities of the leading and terminating electrolytes, causing the stack to stop at a specific location in the channel. According to our unpublished models, by adjusting the $\zeta$ potential within this window, the location of the stack can be changed in a predictable manner, providing a novel means to control the location of the stack on the chip. Thus, a specific zone can be brought within the stack to a stop at a location adjacent to a reaction well or diverter channel and, by switching electrodes, extract all or a portion of the desired zone into the diverter channel for further processing. Then, by switching the electrodes back, the remaining zones can be sent further downstream.

FET-Affinity Chromatography: In this case the protein A is attached to the surface of the $SiO_2$ and contacted against a protein solution containing fluorescently-labeled monoclonal antibodies. After the bound complex has been washed with 3-5 column volumes of equilibration buffer, the "gate" potential is changed in such a way that the pH is dropped below the threshold for antibody release. Detection is the same as in IEF. A key challenge here is that $\zeta$-potential shifts have only been demonstrated in the literature for about 50 mV, giving a predicted pH shift of about 0.4 units in unbuffered solutions and, of course, somewhat less in buffered solutions. A practical application of this technique will require shifts on the order of 1 pH unit in buffered solutions and this is estimated to require $\zeta$-potential shifts on the order of 250 mV.

FET-Electrochromatography: Various different classes of ligands, including those for ion exchange, may respond to a strong shift in the "gate" potential either directly or indirectly as a result of the pH and/or diffuse layer potential shift. Once the protocols for FET-affinity chromatography are established, a number of different classes of stationary phase, including ion exchange, hydrophobic interaction and size exclusion, will be tested using protocols adapted to each separation mechanism. It is expected that the binding affinity of those complexes that involve either a pH or an electrostatic interaction will be affected by shifting the potential.

All patents and publications referenced or mentioned herein are indicative of the levels of skill of those skilled in the art to which the invention pertains, and each such referenced patent or publication is hereby incorporated by reference to the same extent as if it had been incorporated by reference in its entirety individually or set forth herein in its entirety. Applicants reserve the right to physically incorporate into this specification any and all materials and information from any such cited patents or publications.

The specific methods and compositions described herein are representative of preferred embodiments and are exemplary and not intended as limitations on the scope of the invention. Other objects, aspects, and embodiments will occur to those skilled in the art upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. The methods and processes illustratively described herein suitably may be practiced in differing orders of steps, and that they are not necessarily restricted to the orders of steps indicated herein or in the claims. As used herein and in the appended claims, the singular forms "a," "an," and "the" include plural reference unless the context clearly dictates otherwise. Thus, for example, a reference to "a host cell" includes a plurality (for example, a culture or population) of such host cells, and so forth. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed:

1. A device comprising at least one nanochannel, the nanochannel containing a fluid and through which the fluid can move, wherein an ionic double layer forms in the fluid near each wall of the nanochannel and an ionic double layer formed along one wall of the nanochannel substantially overlaps an ionic double layer formed along an opposing wall of the nanochannel; a first electrical potential generating means configured to apply a first electrical potential difference to the fluid at ends of the nanochannel to induce electrokinetic transport along the nanochannel; and a series of second electrical potential generating means connected to electrically isolated portions of the nanochannel wherein each second electrical potential generating means modifies the electrostatic potential distribution across the entire width of a portion of the nanochannel thereby producing an axial pH gradient along the length of the nanochannel.

2. The device of claim 1, wherein at least one portion of one wall of the nanochannel is multilayered with (a) an electrically conducting layer, which can be connected to the second electrical potential, and (b) an insulating or selectively conducting layer which is interposed between the electrically conducting layer and the fluid within the nanochannel.

3. The device of claim 2, wherein the electrically conducting layer is a semi-conductor.

4. The device of claim 2, wherein the electrically conducting layer is metal.

5. The device of claim 2, wherein the multi-layered nanochannel is silicon on insulator.

6. The device of claim 2, wherein multiple electrical potential difference sources are connected between multiple, electrically-isolated portions of the nanochannel wall and fluid at one end of the nanochannel to modify the electrostatic potential distribution within the nanochannel and thereby modify the movement of ions and biomolecules through the nanochannel.

7. The device of claim 6, wherein at least one of the multiple, electrically isolated portions of the nanochannel wall comprise electrically conductive metal.

8. The device of claim 1, wherein at least one nanochannel has a width of about 1 nanometer to about to about 1000 nm.

9. The device of claim 1, wherein at least one nanochannel has a width that changes along the nanochannel's length.

10. The device of claim 9, wherein the width changes from about 10 nm to about 1000 nm along the length of the nanochannel.

11. The device of claim 1, wherein at least one nanochannel is about 50 nanometers to about 10 cm long.

12. The device of claim 1, wherein at least one nanochannel is deeper than it is wide.

13. The device of claim 1, wherein at least one nanochannel is about 10 nanometers to about 2000 nanometers deep.

14. The device of claim 1, comprising an array of about 2 to about 10,000 nanochannels.

15. The device of claim 1, comprising an array of about 10 to about $10^8$ of the nanochannels.

16. The device of claim 1, wherein fluid can flow between at least one nanochannel and at least one microchannel.

17. The device of claim 16, wherein fluid can flow between at least one microchannel and at least one fluid well.

18. The device of claim 17, wherein electrical current can flow through a nanochannel from one well to another well.

19. The device of claim 1, wherein the nanochannel resides in a substrate comprising a semi-conductor.

20. The device of claim 19, wherein the substrate is silicon or germanium.

21. The device of claim 1, wherein nanochannel wall surface charge density is electrically adjusted by changing the second electrical potential difference.

22. The device of claim 1, wherein nanochannel wall surface charge density is chemically adjusted by interaction with a protonating or deprotonating agent.

23. The device of claim 1, wherein nanochannel wall surface charge density is chemically adjusted by interaction with acid or base.

24. The device of claim 1, wherein nanochannel wall surface charge density is chemically adjusted by interaction with hydroxyl ions, amines, ammonium ions, formic acid, barium ions, polylysine, or polyelectrolytes.

25. The device of claim 1, wherein the pH near the nanochannel walls is higher than the pH near the center of the nanochannel.

26. The device of claim 1, wherein the pH near the nanochannel walls is lower than the pH near the center of the nanochannel.

27. The device of claim 1, wherein the average pH difference between the walls and the center of the nanochannel is about 0.01 to about 2.0 pH units.

28. The device of claim 1, wherein the average pH difference between the walls and the center of the nanochannel varies along the nanochannel's length.

29. The device of claim 1, wherein the fluid pH changes as the nanochannel's width changes along the nanochannel's length.

30. The device of claim 1, wherein the fluid pH in at least one nanochannel is different than the fluid pH in at least one second nanochannel.

31. The device of claim 1, wherein the nanochannel is fabricated on a substrate comprising silicon on insulator.

32. The device of claim 1, wherein the device further comprises a two-dimensional array of electrically isolated electrodes under, on top of or in the walls of at least one nanochannel.

33. The device of claim 1, wherein the device further comprises a cover on the nanochannel.

34. The device of claim 33, wherein the cover comprises insulating material.

35. The device of claim 33, wherein the cover comprises material that is transparent to radiation employed a detector for observing molecules that are traveling or have traveled through at least one nanochannel.

36. The device of claim 1, wherein the device further comprises a detector for observing molecules that are traveling or have traveled through at least one nanochannel.

37. The device of claim 1, wherein the device further comprises a detector of fluorescence, light absorption, or light scattering.

38. A network comprising multiple devices, each device consisting essentially of the device of claim 1, and further comprising electronic components that control the first and second electrical potential differences applied to each of the devices, and multiple detectors for observing ionic or molecular transport within each device, wherein the electronic components are interconnected with the detectors to adjust the first and second potential differences in response to the observed ionic or molecular transport within each device.

39. The network of claim 38, wherein the multiple devices are on or within a single substrate.

40. The network of claim 38, wherein the multiple devices are arranged in a two-dimensional or three-dimensional array.

41. The device of claim 1 further comprising a gate oxide having a thickness of approximately 100 nm.

42. The device of claim 1 wherein each electrical potential generating means in the series is individually addressable.

43. The device of claim 1 wherein voltage is applied to the series of electrical potential generating means so as to produce a gradient suitable for isoelectric focusing.

44. The device of claim 1 wherein voltage is applied to the series of electrical potential generating means so as to produce a gradient suitable for isotachophoresis.

45. The device of claim 1 wherein voltage is applied to the series of electrical potential generating means so as to produce a gradient suitable for gradient channel electrophoresis.

46. The device of claim 1 wherein voltage is applied to the series of electrical potential generating means so as to produce a gradient suitable for zone electrophoresis.

47. The device of claim 1 wherein voltage is applied to the series of electrical potential generating means so as to produce a gradient suitable for FET-isotachophoresis.

48. The device of claim 1 wherein voltage is applied to the series of electrical potential generating means so as to produce a gradient suitable for FET-Affinity chromatography.

49. The device of claim 1 wherein voltage is applied to the series of electrical potential generating means so as to produce a gradient suitable for FET-Electrochromatography.

50. The device of claim 1 wherein the electrical potential generating means in the series are positioned at regular intervals along the length of the nanochannel.

51. The device of claim 1 wherein the electrical potential generating means in the series are positioned at irregular intervals along the length of the nanochannel.

52. A method for separating molecules comprising:
flowing a sample comprising the molecules through at least one nanochannel comprising a series of electrical potential generating means distributed in intervals along the length of the nanochannel, wherein an axial pH gradient exists in the at least one nanochannel and an ionic double layer that forms along one wall of the nanochannel substantially overlaps an ionic double layer that forms along an opposing wall of the nanochannel;
applying a first potential difference between fluid at two ends of the at least one nanochannel;
applying a series of electrical potential differences to said to series of electrical potential generating means to modify the electrostatic potential distribution across the entire width of portions of the nanochannel, thereby modifying the axial pH gradient along the length of the nanochannel; and
observing separation of the molecules after portions of the sample have moved at least part way through the at least one nanochannel.

53. The method of claim 52, wherein the sample flows through an interconnected network of nanochannel devices.

54. The method of claim 52, wherein applying the series of second electrical potential differences comprises pulsing an electrical voltage.

55. The method of claim 52, wherein the second electrical potential difference varies along at least one nanochannel.

56. The method of claim 52, wherein observing separation of the molecules comprises employing confocal microscopy.

57. The method of claim 52, wherein observing separation of the molecules comprises detecting a detectable label on a molecule of interest.

58. The method of claim 52, wherein observing separation of the molecules comprises measuring current along a section of the nanochannel.

59. The method of claim 52, wherein observing separation of the molecules comprises amperometry, potentiometry or reflectometry.

60. The method of claim 52, wherein observing separation of the molecules comprises infrared spectroscopy, fluorimetry, light microscopy, ultraviolet microscopy, Fourier transform infrared (FTIR) spectroscopy, nanomachined-waveguide-assisted Fourier transform infrared spectroscopy (NWA-FTIRS), or electrochemical impedance spectroscopy (EIS).

61. The method of claim 52 further comprising applying a voltage to the series of electrical potential generating means so as to produce a gradient suitable for isoelectric focusing; and performing isoelectric focusing on the molecules.

62. The device of claim 52 further comprising applying a voltage to the series of electrical potential generating means so as to produce a gradient suitable for isotachophoresis and performing isotachophoresis on the molecules.

63. The device of claim 52 further comprising applying a voltage to the series of electrical potential generating means so as to produce a gradient suitable for gradient channel electrophoresis and performing gradient channel electrophoresis on the molecules.

64. The device of claim 52 further comprising applying a voltage to the series of electrical potential generating means so as to produce a gradient suitable for zone electrophoresis and performing zone electrophoresis on the molecules.

65. The device of claim 52 further comprising applying a voltage to the series of electrical potential generating means so as to produce a gradient suitable for FET-isotachophoresis and performing FET-isotachophoresis on the molecules.

66. The device of claim 52 further comprising applying a voltage to the series of electrical potential generating means so as to produce a gradient suitable for FET-Affinity chromatography and performing FET-Affinity chromatography on the molecules.

67. The device of claim 52 further comprising applying a voltage to the series of electrical potential generating means so as to produce a gradient suitable for FET-Electrochromatography and performing FET-Electrochromatography on the molecules.

68. A device comprising:
an array of nanochannels having two ends;
each nanochannel having:
an electrically conductive portion, such that when coupled to a difference in potential, an ionic double layer forms in fluid near the electrically conductive portion of the nanochannel and an ionic double layer formed along one wall of the nanochannel substantially overlaps an ionic double layer formed along an opposing wall of the nanochannel; and
a pH gradient across the width of the nanochannel;
a microfluidic interface at an end of the array of nanochannels for providing the fluid to the nanochannels; and
each nanochannel having at least one electrode present along the nanochannel, wherein the electrode applies an electrical potential difference so as to shift the pH of the fluid distribution across the entire width of at least a portion of the nanochannel and thereby modify the movement of the ions and molecules through the nanochannel.

69. A device for performing isoelectric focusing comprising:
at least one nanochannel containing a fluid and through which the fluid can move, wherein an ionic double layer forms in the fluid near each wall of the nanochannel and an ionic double layer formed along one wall of the nanochannel substantially overlaps an ionic double layer formed along an opposing wall of the nanochannel; a first electrical potential generating means configured to apply a first electrical potential difference to the fluid at ends of the nanochannel to induce electrokinetic transport along the nanochannel; and a series of electrical potential generating means distributed at intervals along the length of the nanochannel configured to produce an axial gradient in the electrical potential and/or the electric current along the length of the nanochannel, and wherein at least one of the electrical potential generating means in the series produces a pH gradient across the width of the nanochannel.

* * * * *